(12) United States Patent
Dilmaghanian et al.

(10) Patent No.: US 10,535,945 B2
(45) Date of Patent: Jan. 14, 2020

(54) CANTED COIL SPRINGS, CONNECTORS AND RELATED METHODS

(71) Applicant: Bal Seal Engineering, Inc., Foothill Ranch, CA (US)

(72) Inventors: Farshid Dilmaghanian, Rancho Santa Margarita, CA (US); Peter J. Balsells, Newport Beach, CA (US); Majid Ghasiri, Mission Viejo, CA (US); Lluis Soler, Irvine, CA (US); Derek Changsrivong, Costa Mesa, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 0 days.

(21) Appl. No.: 15/285,350

(22) Filed: Oct. 4, 2016

(65) Prior Publication Data

US 2017/0025779 A1    Jan. 26, 2017

Related U.S. Application Data

(63) Continuation of application No. 14/855,288, filed on Sep. 15, 2015, now Pat. No. 10,270,198.
(Continued)

(51) Int. Cl.
*F16B 21/18* (2006.01)
*F16F 1/04* (2006.01)
(Continued)

(52) U.S. Cl.
CPC ......... *H01R 13/2421* (2013.01); *F16B 21/18* (2013.01); *H01R 13/187* (2013.01);
(Continued)

(58) Field of Classification Search
CPC ..... A61N 1/3752; F16B 21/18; F16B 21/183; F16B 21/186; F16F 1/042; F16F 1/043;
(Continued)

(56) References Cited

U.S. PATENT DOCUMENTS

| 501,560 | A | * | 7/1893 | Cooper et al. | ............. | F16J 9/06 |
| | | | | | | 267/167 |
| 1,867,723 | A | * | 7/1932 | Adams | ................... | D06F 83/00 |
| | | | | | | 267/167 |

(Continued)

FOREIGN PATENT DOCUMENTS

| DE | 19807663 | 9/1999 |
| EP | 2497527 A2 | 9/2012 |

(Continued)

OTHER PUBLICATIONS

International Search Report and Written Opinion on related PCT application (PCT/US2015/050283) from International Searching Authority (KR) dated Jan. 8, 2016.

(Continued)

*Primary Examiner* — Josh Skroupa
(74) *Attorney, Agent, or Firm* — Klein, O'Neill & Singh, LLP

(57) ABSTRACT

Connector assemblies formed by attaching two stamped housing sections to form a connector housing having a housing groove with a groove bottom and two side walls are disclosed. Using stamped housing sections can reduce manufacturing costs and simplifies assembly, among other things. The connector housings with a canted coil spring can be used as a mechanical connector and/or as an electrical connector for numerous applications and across numerous industries. The canted coil springs can have complex shapes, with optional dimples.

19 Claims, 13 Drawing Sheets

Related U.S. Application Data

(60) Provisional application No. 62/050,457, filed on Sep. 15, 2014, provisional application No. 62/161,925, filed on May 15, 2015.

(51) Int. Cl.
*H01R 13/24* (2006.01)
*H01R 13/514* (2006.01)
*H01R 13/187* (2006.01)
*A61N 1/375* (2006.01)
*H01R 13/18* (2006.01)
*H01R 13/504* (2006.01)

(52) U.S. Cl.
CPC .......... *H01R 13/514* (2013.01); *A61N 1/3752* (2013.01); *F16F 1/045* (2013.01); *H01R 13/504* (2013.01); *H01R 2201/12* (2013.01); *Y10T 403/60* (2015.01)

(58) Field of Classification Search
CPC .... F16F 1/045; F16F 1/12; F16F 1/127; F16L 37/22; H01R 13/187; H01R 13/2421; H01R 13/514; Y10T 403/4637; Y10T 403/60; Y10T 403/602; Y10T 403/604; Y10T 403/64; Y10T 403/7073
USPC ........... 403/243, 326–328, 335, 375, DIG. 7, 403/DIG. 14; 267/167, 180
See application file for complete search history.

(56) References Cited

U.S. PATENT DOCUMENTS

| | | | |
|---|---|---|---|
| 3,174,500 A | 3/1965 | Johnson et al. | |
| 4,655,462 A | 4/1987 | Balsells | |
| 4,678,210 A | 7/1987 | Balsells | |
| 4,826,144 A | 5/1989 | Balsells | |
| 4,830,344 A | 5/1989 | Balsells | |
| 4,872,710 A | 10/1989 | Konecny et al. | |
| 4,876,781 A | 10/1989 | Balsells | |
| 4,893,795 A | 1/1990 | Balsells | |
| 4,907,788 A | 3/1990 | Balsells | |
| 4,915,366 A | 4/1990 | Balsells | |
| 4,934,666 A | 6/1990 | Balsells | |
| 4,961,253 A | 10/1990 | Balsells | |
| 4,964,204 A | 10/1990 | Balsells | |
| 4,974,821 A | 12/1990 | Balsells | |
| 5,108,078 A | 4/1992 | Balsells | |
| 5,139,243 A | 8/1992 | Balsells | |
| 5,139,276 A | 8/1992 | Balsells | |
| 5,149,642 A | 9/1992 | Mazur et al. | |
| 5,160,122 A | 11/1992 | Balsells | |
| 5,203,849 A | 4/1993 | Balsells | |
| 5,239,737 A | 8/1993 | Balsells | |
| 5,411,348 A | 5/1995 | Balsells | |
| 5,503,375 A | 4/1996 | Balsells | |
| 5,545,842 A | 8/1996 | Balsells | |
| 5,570,719 A | 11/1996 | Richards et al. | |
| 5,709,371 A | 1/1998 | Balsells | |
| 5,791,638 A | 8/1998 | Balsells | |
| 6,672,565 B2 | 1/2004 | Russell | |
| 6,835,084 B2 | 12/2004 | Poon et al. | |
| 7,055,812 B2 | 6/2006 | Balsells | |
| 7,299,095 B1* | 11/2007 | Barlow ................ | H01R 13/187 607/36 |
| 7,538,289 B2 | 5/2009 | Carroll | |
| 7,722,415 B2 | 5/2010 | Changsrivong | |
| 7,914,315 B2 | 3/2011 | Kuhn et al. | |
| 7,914,351 B2 | 3/2011 | Balsells et al. | |
| 7,985,105 B2 | 7/2011 | Balsells | |
| 8,052,459 B2 | 11/2011 | Smith et al. | |
| 8,096,842 B2 | 1/2012 | Poon et al. | |
| 8,167,285 B2* | 5/2012 | Balsells ................. | F16B 21/18 403/326 |
| 8,308,167 B2 | 11/2012 | Balsells et al. | |
| 8,336,864 B2 | 12/2012 | Noh | |
| 8,382,532 B2 | 2/2013 | Sjostedt et al. | |
| 8,428,724 B2 | 4/2013 | Sage | |
| 8,491,346 B2 | 7/2013 | Sjostedt et al. | |
| 8,561,274 B2 | 10/2013 | Balsells | |
| 8,590,867 B2 | 11/2013 | Leon | |
| 9,004,805 B2 | 4/2015 | Changsrivong et al. | |
| 9,010,740 B2* | 4/2015 | Jaster ..................... | F16F 1/045 267/167 |
| 9,267,526 B2 | 2/2016 | Balsells | |
| 9,273,742 B2 | 3/2016 | Balsells et al. | |
| 9,284,970 B2 | 3/2016 | Dilmaghanian et al. | |
| 9,293,849 B2* | 3/2016 | Balsells ............ | H01R 13/2421 |
| 9,312,630 B2 | 4/2016 | Huang | |
| 9,482,255 B2 | 11/2016 | Changsrivong et al. | |
| 9,500,211 B2 | 11/2016 | Changsrivong | |
| 9,518,626 B2 | 12/2016 | Balsells et al. | |
| 9,534,625 B2 | 1/2017 | Balsells | |
| 9,677,587 B2 | 6/2017 | Changsrivong et al. | |
| 2001/0018298 A1* | 8/2001 | Nakamura ........... | H01R 13/187 439/841 |
| 2002/0122690 A1 | 9/2002 | Poon et al. | |
| 2003/0096526 A1 | 5/2003 | Balsells | |
| 2005/0234521 A1 | 10/2005 | Balsells | |
| 2006/0228166 A1 | 10/2006 | Balsells | |
| 2009/0258519 A1 | 10/2009 | Dilmaghanian et al. | |
| 2010/0279558 A1 | 11/2010 | Leon et al. | |
| 2010/0289198 A1 | 11/2010 | Balsells et al. | |
| 2011/0062640 A1* | 3/2011 | Leon ....................... | F16F 1/045 267/166 |
| 2011/0280653 A1* | 11/2011 | Sjostedt ............... | H01R 13/187 403/361 |
| 2011/0281476 A1 | 11/2011 | Sjostedt et al. | |
| 2012/0098179 A1* | 4/2012 | Jaster ..................... | F16F 1/045 267/166 |
| 2012/0174398 A1 | 7/2012 | Rust et al. | |
| 2012/0295471 A1 | 11/2012 | Leon | |
| 2013/0149031 A1 | 6/2013 | Changsrivong et al. | |
| 2014/0079476 A1 | 3/2014 | Dilmaghanian et al. | |
| 2014/0130329 A1 | 5/2014 | Changsrivong et al. | |
| 2014/0162487 A1 | 6/2014 | Frederick et al. | |
| 2014/0259617 A1 | 9/2014 | Kompa et al. | |
| 2014/0378008 A1 | 12/2014 | Young et al. | |
| 2015/0240900 A1 | 8/2015 | Poon et al. | |
| 2015/0316115 A1 | 11/2015 | Carter | |
| 2016/0076568 A1 | 3/2016 | Dilmaghanian et al. | |
| 2016/0204557 A1 | 7/2016 | Kim | |
| 2016/0265574 A1 | 9/2016 | Ghasiri | |
| 2017/0352984 A1 | 12/2017 | Changsrivong et al. | |
| 2017/0373425 A1 | 12/2017 | Rust | |

FOREIGN PATENT DOCUMENTS

| | | |
|---|---|---|
| GB | 2194298 | 3/1988 |
| WO | WO 03067713 | 8/2003 |

OTHER PUBLICATIONS

Non-Final Office Action on co-pending U.S. Appl. No. 14/855,288 dated Mar. 30, 2018.

Extended European Search Report from European Patent Office on co-pending EP application (EP15841236.1) dated Jun. 12, 2018.

Beringer-Ney, "Cold Forming and Cold Heading Process," https://web.archive.org/web/20131203110117/http://www.deringerney.com/products-and-capabilities/cold-forming/cold-forming-process/, Dec. 3, 2013.

Final Office Action on co-pending U.S. Appl. No. 14/855,288 dated Oct. 29, 2018.

* cited by examiner

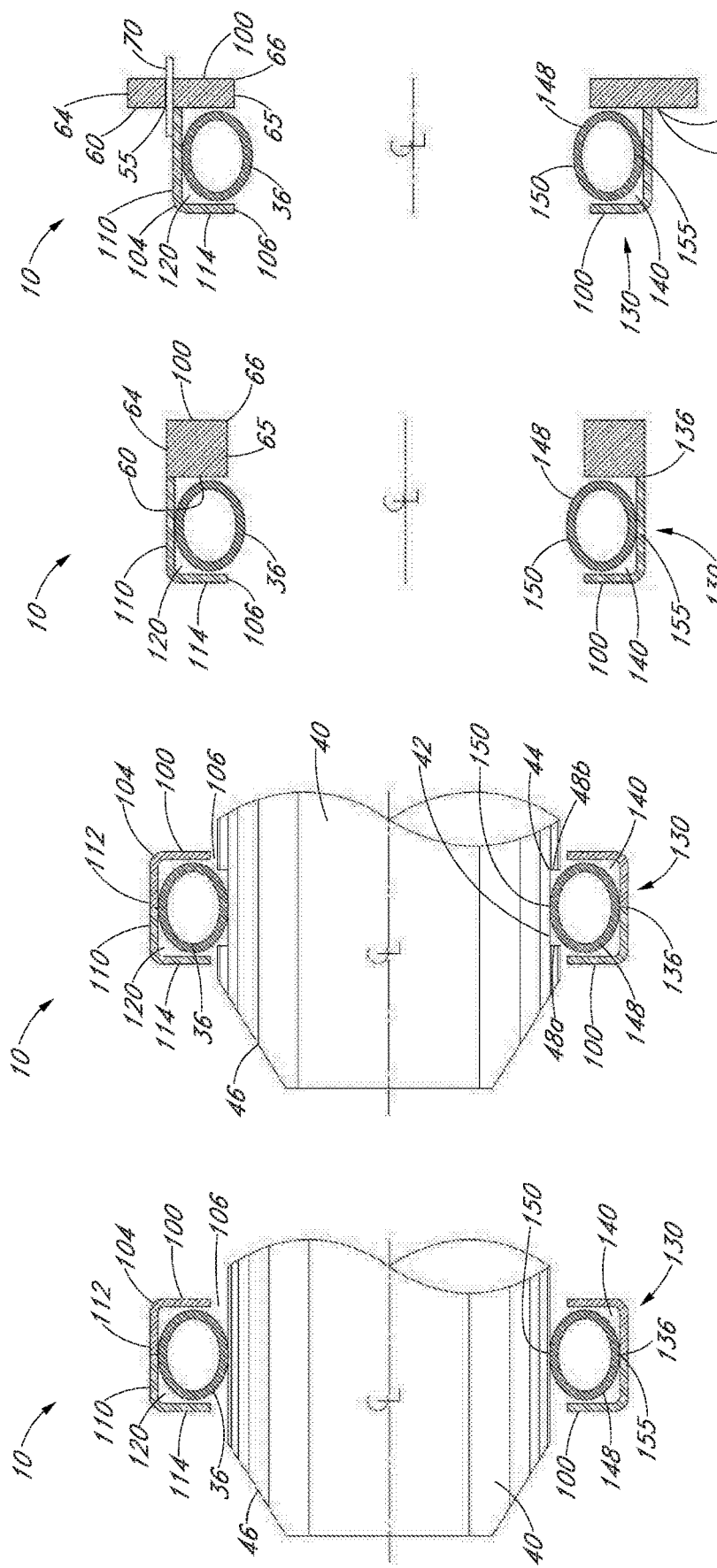

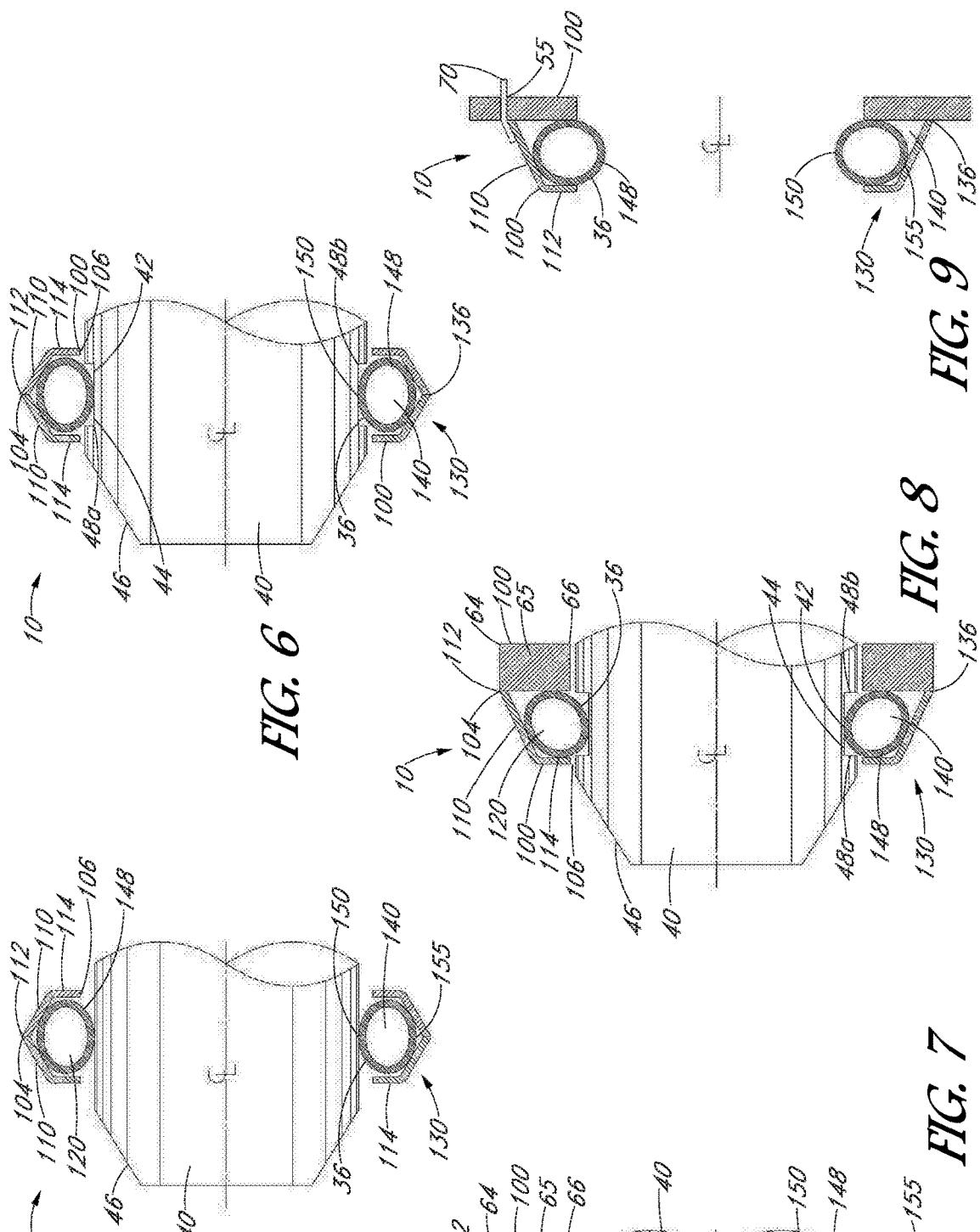

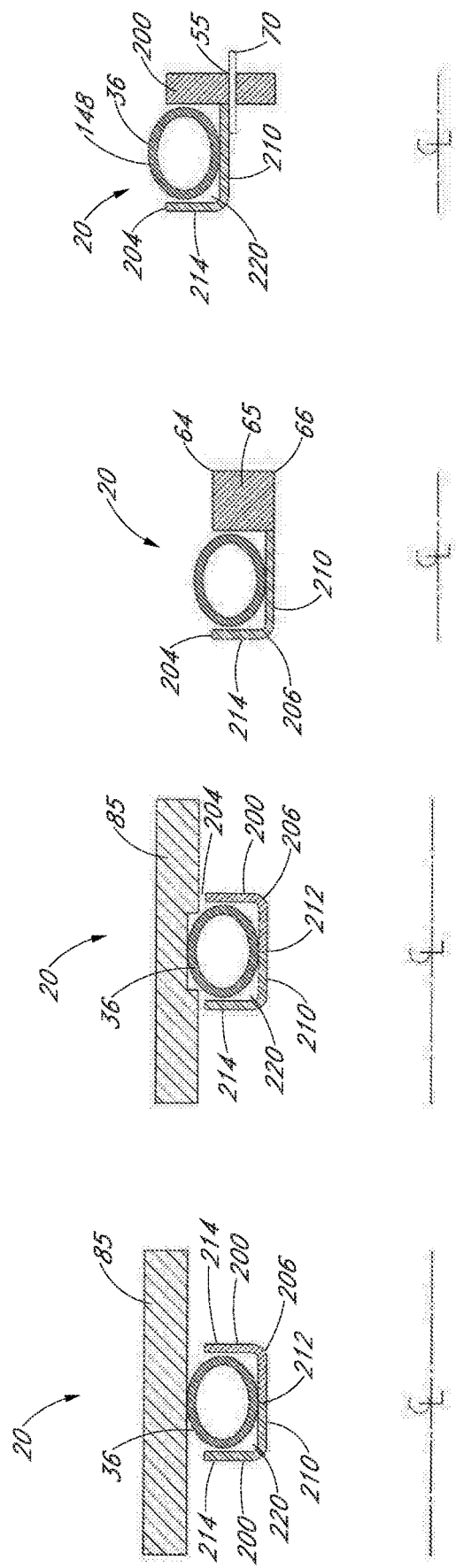
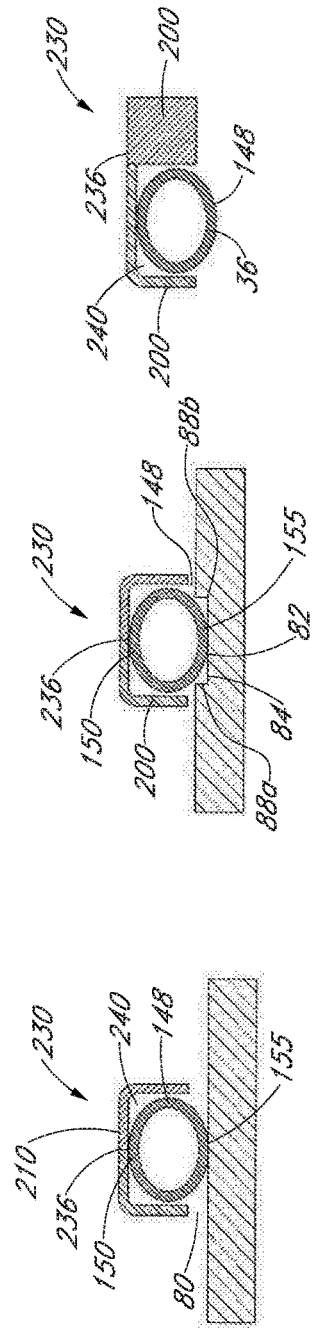
FIG. 10  FIG. 11  FIG. 12  FIG. 13

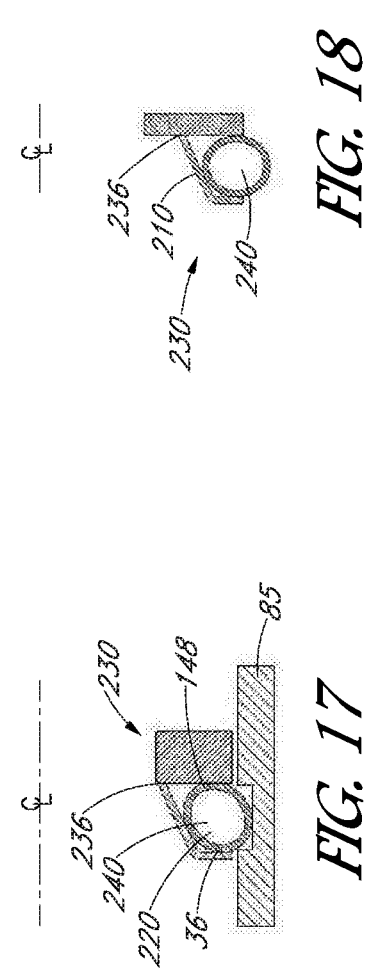
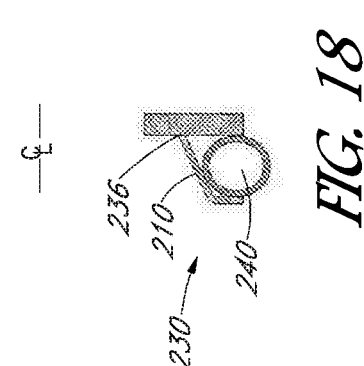
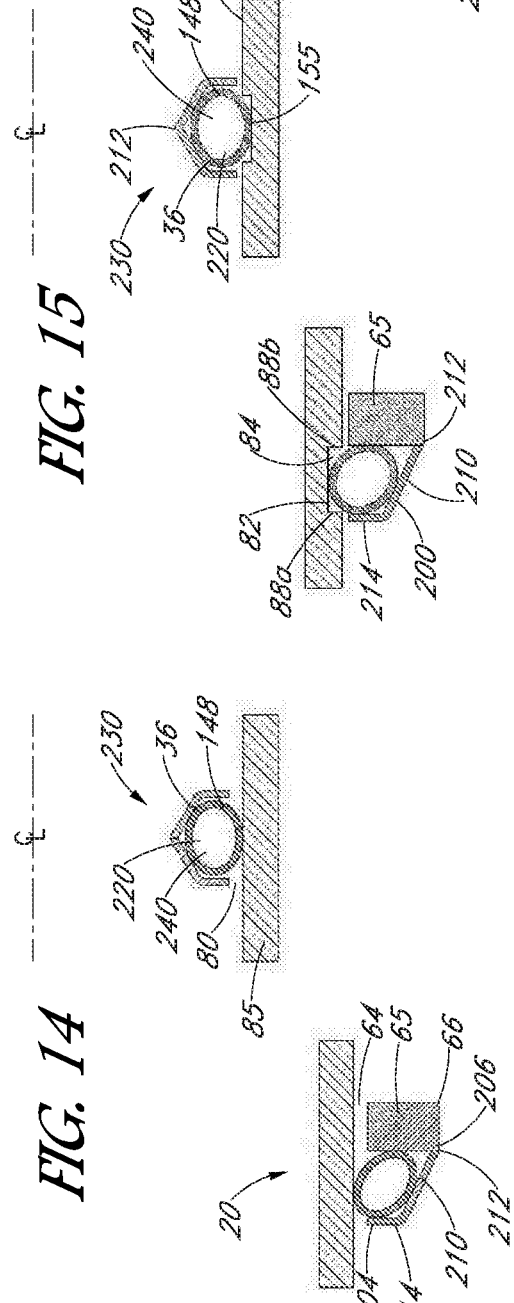
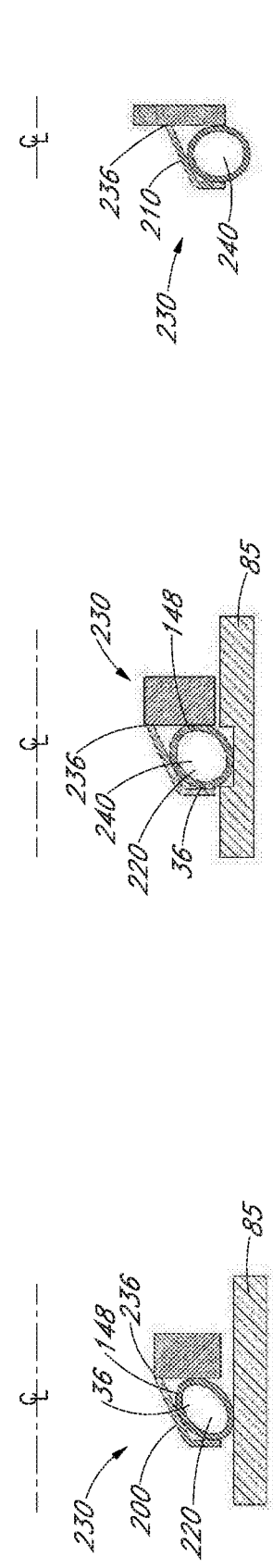

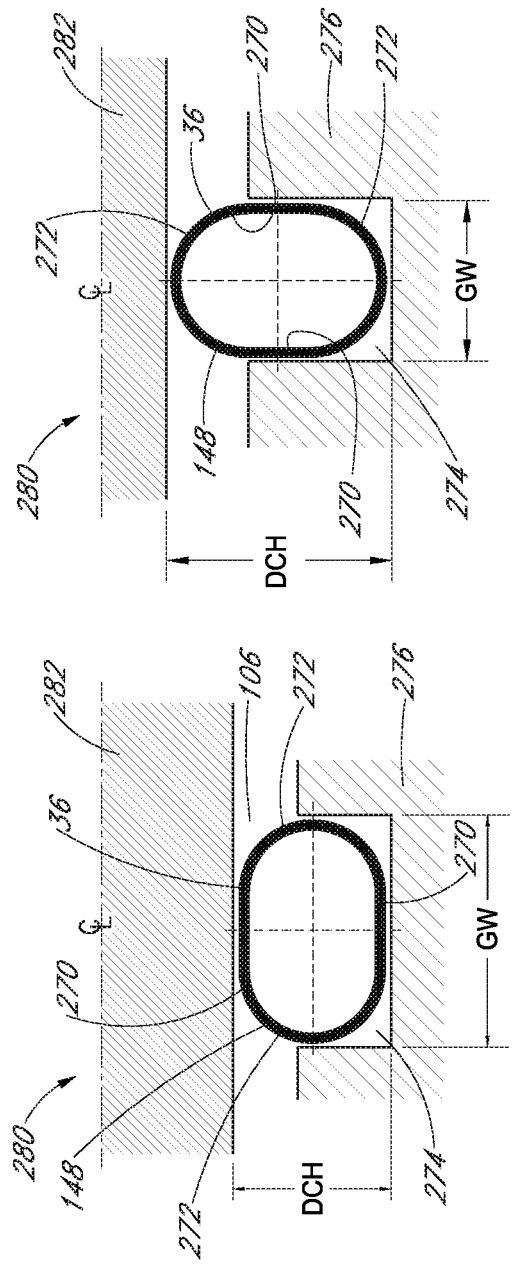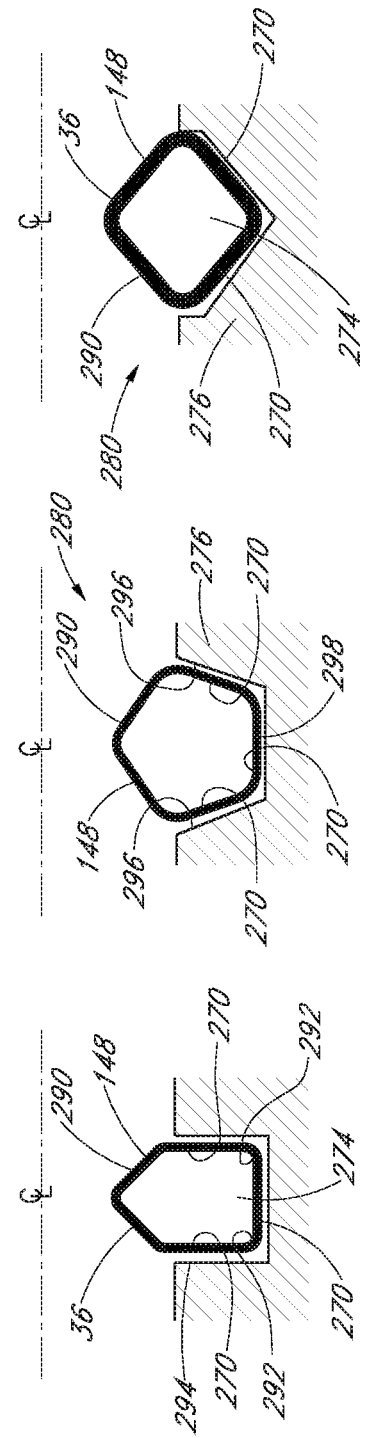
FIG. 19A  FIG. 19B
FIG. 20A  FIG. 20B  FIG. 20C

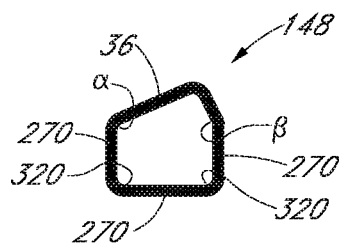
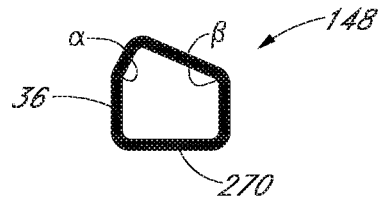
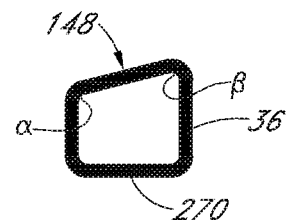
FIG. 23A          FIG. 23B          FIG. 23C
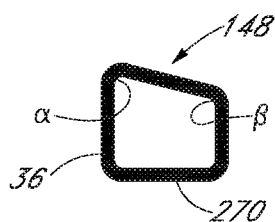
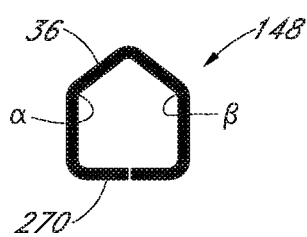
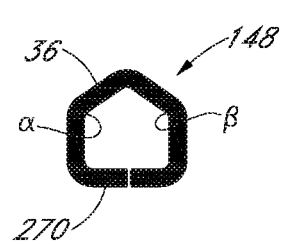
FIG. 23D          FIG. 23E          FIG. 23F
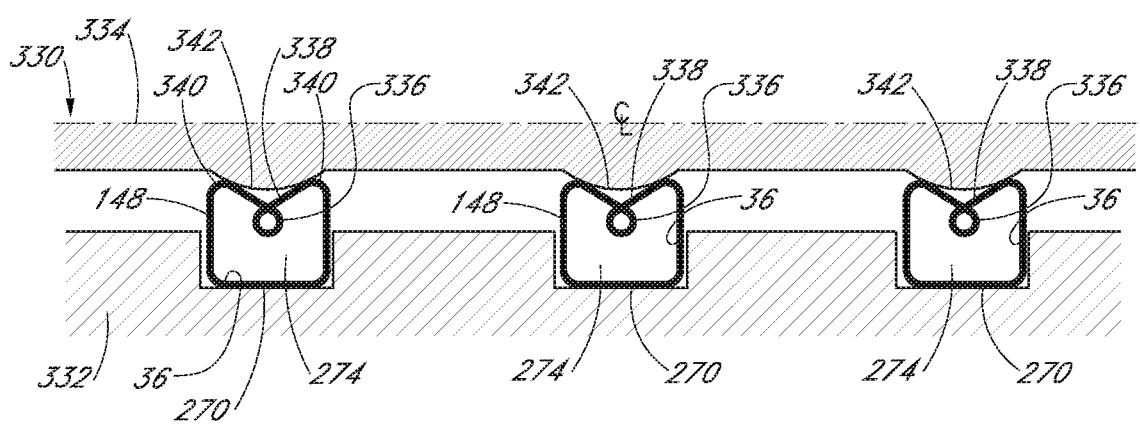
FIG. 24

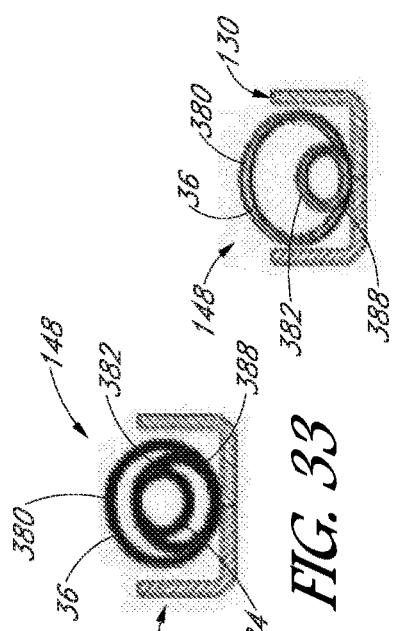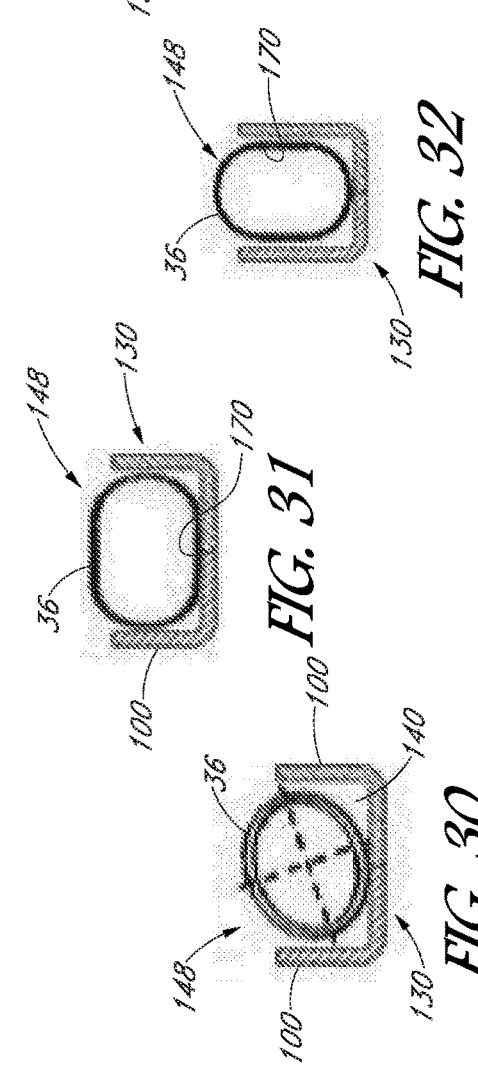

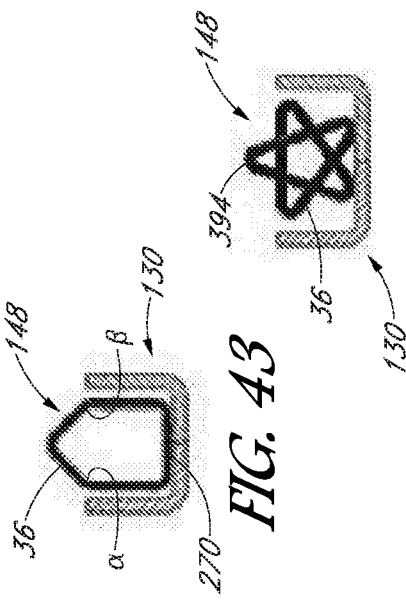
FIG. 40
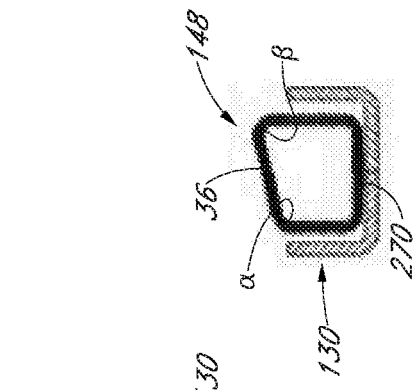
FIG. 41
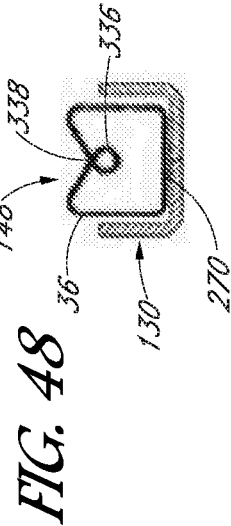
FIG. 42
FIG. 43
FIG. 44
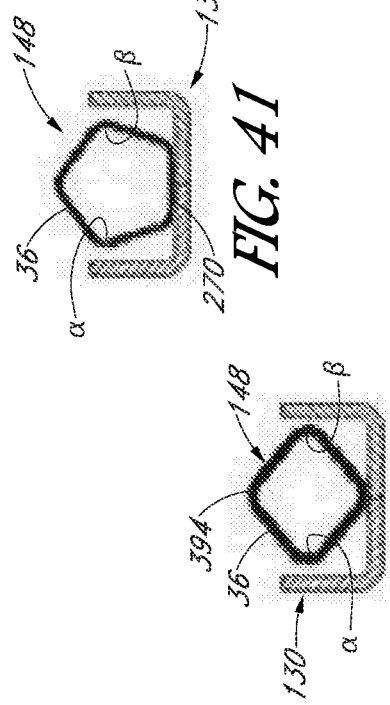
FIG. 45
FIG. 46
FIG. 47
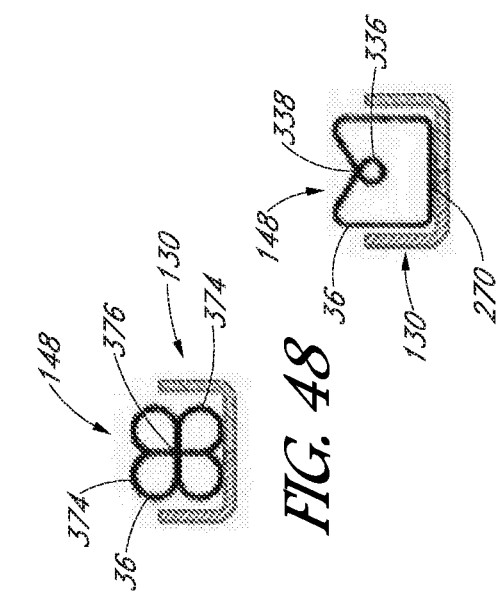
FIG. 48
FIG. 49

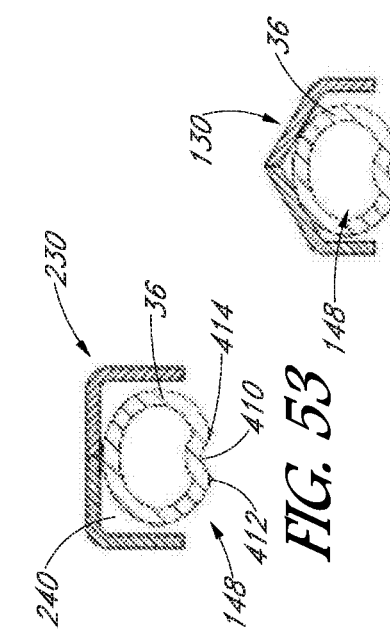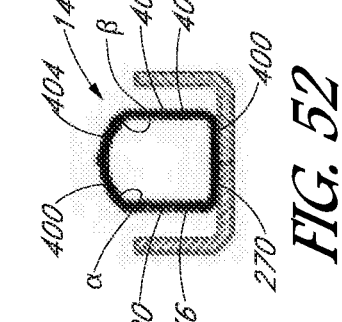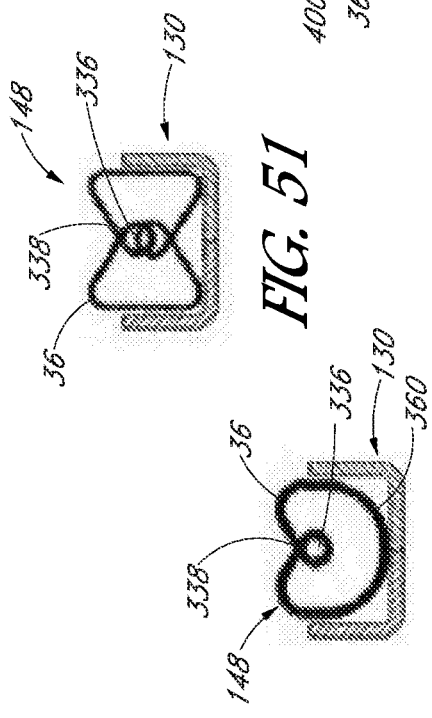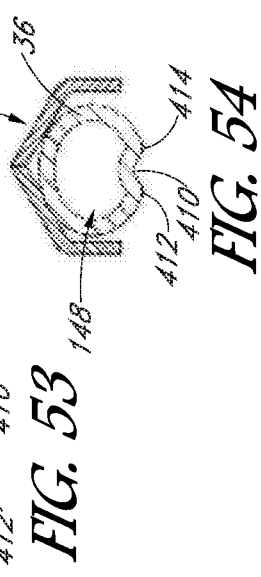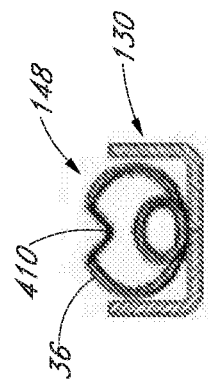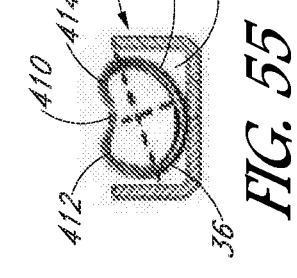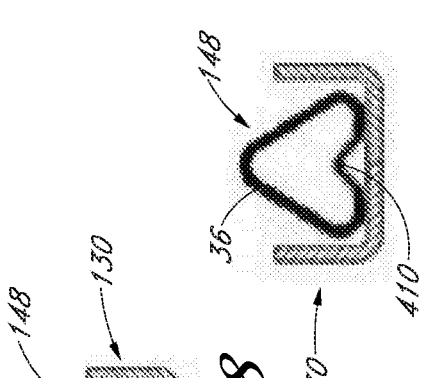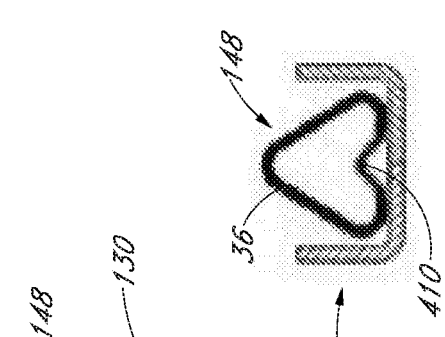

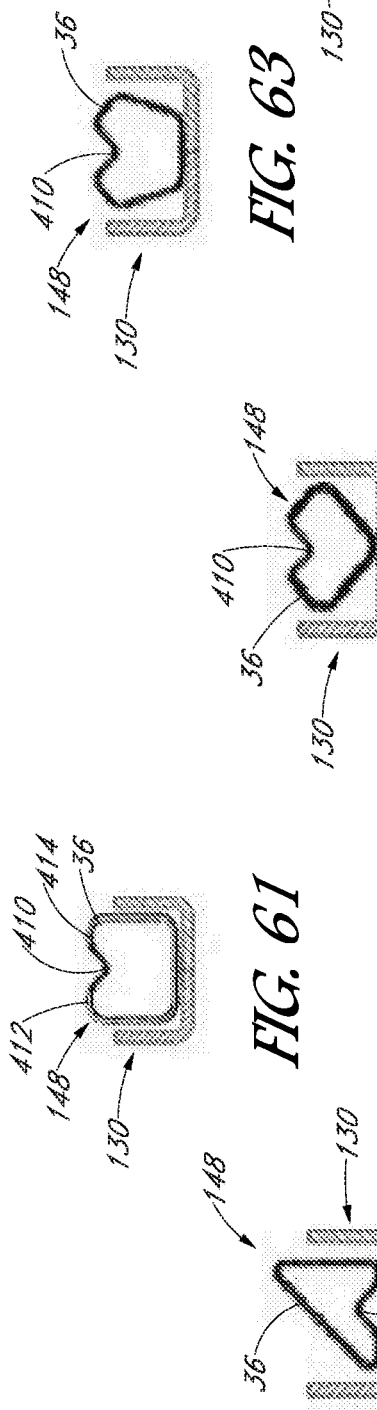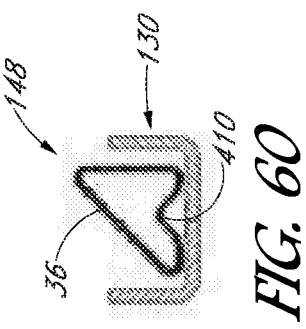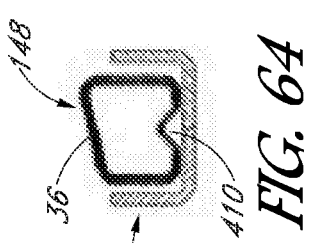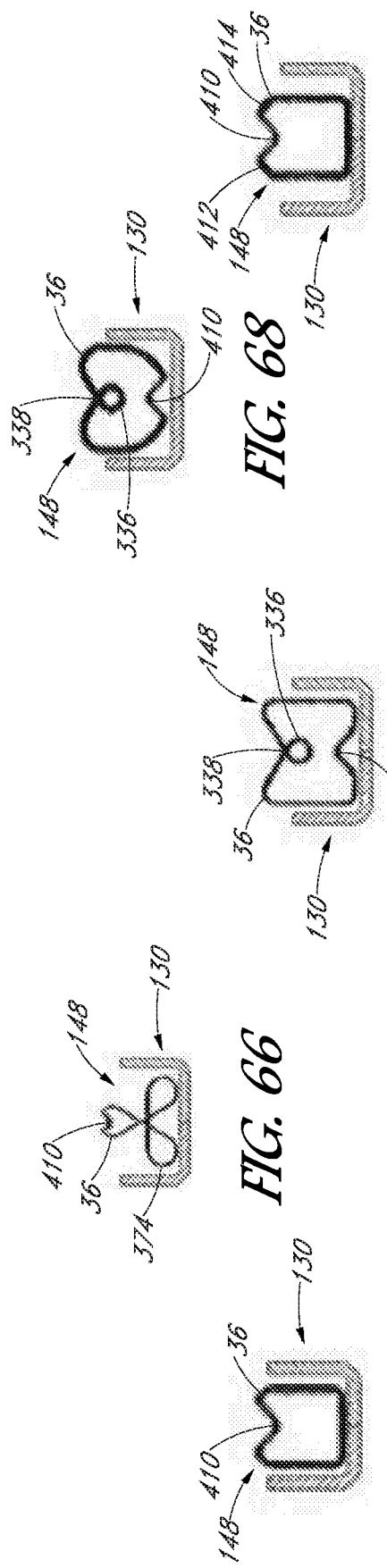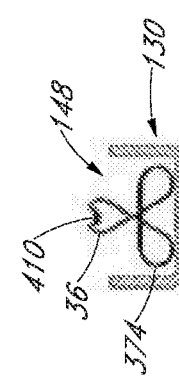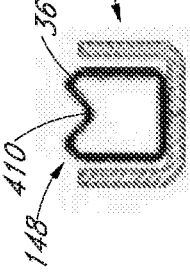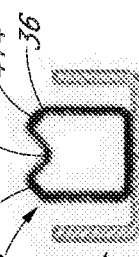

CANTED COIL SPRINGS, CONNECTORS AND RELATED METHODS

CROSS-REFERENCE TO RELATED APPLICATION

This is a continuation of co-pending application Ser. No. 14/855,288, filed Sep. 15, 2015, which claims priority to provisional application Ser. No. 62/050,457, filed Sep. 15, 2014, and provisional application Ser. No. 62/161,925, filed May 15, 2015, the contents of which are expressly incorporated herein by reference.

FIELD OF ART

The present disclosure generally relates to canted coil springs and their applications, such as in connector applications having a connector housing and a pin and more particularly to connector housings made from stamped housing sections, stamped housing sections as part of a mechanical connector, as part of an electrical connector, in a medical application, and as methods for forming and using the stamped housing sections.

BACKGROUND

Implantable stackable lead connectors to date consist of a series of machined housings, also referred to as conductive contacts, separated by sealing members and wherein a spring contact is held in a groove defined at least in part by each machined housing section. Due to tolerance concerns and critical dimension constraints, the housing components may need to be precision machined, resulting in a high cost connector. Furthermore, as the size of the connectors decrease, the housings become very difficult to machine. Exemplary implantable medical connectors are discussed in U.S. Pat. No. 8,437,855, the contents of which are expressly incorporated herein by reference for purposes of generally disclosing IMDs and in-line connectors used with IMDs and components for forming or making in-line connectors.

Connectors are also known for use as mechanical fasteners, as electrical connectors, as latching connectors, as holding connectors and as locking connectors. These connectors typically have a housing with a bore and a pin either with or without a pin groove. A spring is placed in the groove, either of the housing or the pin, for forming a connection between the pin and the housing, which can be a holding connection type, a latching connection type in which the pin is allowed to be removed from the housing, or a locking connection type in which the pin is not allowed to be removed from the housing unless the connector, such as the spring, is destroyed. When the housing and the pin are coupled to an electrical source or node to pass current or electrical signals there-across, the connector can also carry current and functions as an electrical connector. Exemplary connectors are disclosed in U.S. Pat. Nos. 4,678,210; 5,082,390; 5,411,348; and 8,297,662.

SUMMARY

Aspects of the present disclosure include a connector with spring contact housings formed from stamped components to achieve low manufacturing costs, reduced connector length, reduced stress and chance of mis-orientation of the spring contact when installed into the housing. The connector can also include testing capabilities to confirm proper performance prior to completing assembly of the housing. Although the housings have contours and shapes that are formed by cold working and pressure, some part or parts of the housing may optionally be machined.

Due to the nature of stamped components, the housing components can be made with very consistent dimensions and thinner when compared to machined housings, which may reduce the overall length of the connector and potentially reduce the size of the implantable device or other small applications.

The multi-piece housings described herein can allow the spring contacts, such as canted coil springs, to be installed within the housing assemblies with reduced deflection, stress, mis-orientation, or combinations thereof. Furthermore, multi-piece housings can allow for proper placement and performance of spring contacts within the multi-piece housings to be tested, adjusted, and confirmed before the housing is completely assembled.

A further feature of the present disclosure is an in-line series of stackable contact assemblies that can be used with sealing members, each contact assembly comprising a housing and a spring, the housing being formed from at least one stamped component being joined to a surface or another stamped component and forming a groove in which the spring contact is retained. Exemplary stackable components used with sealing members are disclosed in U.S. Publication No. 2014/0079476, the contents of which are expressly incorporated herein by reference to disclose stackable in-line features and encapsulation layers for use with connector housings disclosed herein and canted coil springs disclosed herein.

The connector whereby the housing can be formed from two identical stamped components joined together. In other examples, the two stamped housing sections that are joined are not identical. In yet other examples, the housing can be joined to a surface, such as a housing body with planar surfaces and an opening.

The connector whereby the components that form the housing can be joined together by welding or physically supporting.

The connector whereby the housing can have an exterior groove or an interior groove to support a spring.

The connector wherein the housing section can be connected to an electrical lead.

The connector whereby the groove can be used for linear positioning of components within the connector.

The connector whereby the groove bottom can be flat and can contact a canted coil spring having a plurality of coils and wherein the plurality of coils each has a dimple to form two contact points with the groove bottom compared to a single point when no dimple is formed on a curved surface.

The connector whereby the spring can be a canted coil spring, a garter spring, a cantilever spring, or a ribbon spring.

Another feature of the present disclosure is a method of testing the performance of a spring contact of a connector. The method can comprise the step of obtaining an in-line series of stackable contact assemblies and sealing members, each contact assembly comprising a housing and a spring contact, the housing being formed from at least one stamped component being joined to another component and forming a groove in which the spring contact is retained, prior to complete assembly of the housing by holding the components that form the housing together with the spring contact installed in the housing and inserting a lead to find insertion, removal, and frictional forces, and electrical performance.

The connector assembly wherein both housing sections can be formed from a blank in a stamping process.

The connector assembly can further comprise a canted coil spring located in the housing groove. The canted coil spring can have coils having a variety of different shapes, other than elliptical and rectangular, and can optionally include a dimple or two dimples formed on each coil. The dimple can be formed by creating a concave bend along an arc section of the coil or by forming an internal or interior loop.

The connector assembly wherein the canted coil spring can have a smaller inside diameter than diameters of the two openings defining the common bore of the housing.

The connector assembly wherein the canted coil spring can have a larger inside diameter than a diameter of a housing bore.

The connector assembly can further comprise a pin projecting through the common bore and the spring center.

The connector assembly can further comprise a seal element having a bore with a seal lip, said seal element abutting the connector housing and sealingly located inside a header of an implantable medical device.

The connector assembly can further comprise a second connector housing abutting the seal element and a second seal element abutting the second connector housing; and wherein said second connector housing has a canted coil spring located therein.

The connector assembly wherein the interface of the housing sections or between a housing section and a surface can be welded.

The connector assembly can further comprise a header attached to a can housing of an implantable medical device, and wherein the connector housing can be disposed inside the header adjacent a seal element having a bore aligned with the common bore.

The connector assembly wherein said first housing section and said second housing section can be identical.

The connector assembly wherein said connector housing can form a U-shaped groove or a V-shaped groove.

Yet another feature of the present disclosure is a method for making a connector housing comprising stamping a first housing section and stamping a second housing section. The method can further comprise placing a canted coil spring inside said first housing section and attaching said first housing section to said second housing section to form a connector housing comprising a common bore and a housing groove comprising a groove bottom and two sidewalls. The groove bottom can be flat, such as forming an orthogonal surface with the sidewalls, or can be tapered relative to the sidewalls.

Another method for making a connector housing comprises stamping a first housing section, placing a canted coil spring inside said first housing, and attaching said first housing section to a surface of a housing body, which does not have to be cold worked with a die, to form a connector housing comprising a common bore and a housing groove comprising a groove bottom and two side walls.

The method wherein said canted coil spring can be placed in the housing groove after said attaching step or before said attaching step.

The method can further comprise the step of placing said connector housing in contact with a seal element and into a header of an implantable medical device.

The method can further comprise placing said connector housing in contact with a seal element and into an encapsulation layer to form an encapsulated stack.

A further feature of the present disclosure is a connector assembly comprising a connector housing comprising a first housing section attached to a second housing section and having an interior cavity with a housing groove comprising a groove bottom. The housing groove can further comprise one or two sidewalls. If one sidewall, the bottom surface can be slanted and extend into one of the two openings of the housing bore. The first housing section can comprise a first bottom wall with an endmost surface and/or a first sidewall coupled to the first bottom wall at an angle. The second housing section can comprise a second bottom wall with an endmost surface and/or a first sidewall coupled to the first bottom wall at an angle. The second housing section can also be a contact surface. The housing groove can be cooperatively defined by the first and second bottom walls attached to one another at their respective endmost surfaces or the endmost surface of the first bottom wall attached to the contact surface.

The connector assembly wherein the first housing section and the second housing section can be substantially identical.

The connector assembly wherein the first and second housing sections can each have a bore and the first and second sidewalls extend inwardly to define two bores.

The connector assembly can further comprise a canted coil spring located in the housing groove. The canted coil spring can have a smaller inside diameter than the bores of the housing sections. The canted coil spring can have coils with shapes other than elliptical and rectangular. The coils can optionally have one or two dimples.

The connector assembly can further comprise a pin projecting through the bores of the housing sections and the inside diameter of the canted coil spring can be smaller than a nominal diameter of the pin.

The connector assembly wherein an outer perimeter of the connector housing can be circular and the first and second sidewalls can extend outwardly to define an external groove.

The connector assembly can further comprise a canted coil spring located in the external groove, wherein the canted coil spring can have a larger outside diameter than outer perimeters of the housing sections.

The connector assembly can further comprise an external housing having a bore. The bore can have a smaller nominal diameter than the outside diameter of the canted coil spring.

The connector assembly wherein an angle between the bottom wall and the sidewall of the housing section can be substantially perpendicular.

The connector assembly wherein an angle between the bottom wall and the sidewall of the housing section can be an obtuse angle.

The connector assembly wherein the first and second housing can be attached together by welding or held together by an encapsulation layer.

Another feature of the present disclosure is a connector assembly comprising a connector housing comprising a housing section attached to a contact surface of a body and having an interior cavity with a housing groove comprising a groove bottom. The housing groove can further have a sidewall coupled to the groove bottom opposite the contact surface. The housing section can comprise a bottom wall having an end most surface and/or a sidewall coupled to the bottom wall at an angle. The housing groove can be cooperatively defined by the end most surface of the bottom wall of the housing section attached to the surface. The connector assembly wherein the housing section can have a bore, and the sidewall can extend inwardly to define the bore.

The connector assembly can further comprise a canted coil spring located in the housing groove, wherein the canted coil spring can have a smaller inside diameter than the bore of the housing section and the body. The canted coil spring can have coils with shapes other than elliptical and rectangular. The coils can optionally have one or two dimples.

The connector assembly of claim can further comprise a pin projecting through the bores of the housing section and the body, and the inside diameter of the canted coil spring is smaller than a nominal diameter of the pin.

The connector assembly of claim wherein an outer perimeter of the connector housing can be circular, and the first and second sidewalls can extend outwardly to define an external groove.

The connector assembly can further comprise a canted coil spring located in the external groove, wherein the canted coil spring can have a larger outside diameter than outer perimeters of the housing section and the body.

The connector assembly can further comprise an external housing having a bore, wherein the bore of the external housing can have a smaller nominal diameter than the outside diameter of the canted coil spring.

The connector assembly wherein an angle between the bottom wall and the sidewall of the housing section can be substantially perpendicular.

The assembly wherein the housing groove can be V-shaped without sidewalls.

The connector assembly can further comprise a lead passing through an opening through the surface of the body and electrically connecting to the housing section.

Yet another feature of the present disclosure is a method for making a connector housing. The method can comprise stamping a first housing section, the first housing section can comprise a first bottom wall having an end most surface and a first sidewall coupled to the first bottom wall at an angle to define a first recessed space.

The method can further comprise stamping a second housing section, the second housing section can comprise a second bottom wall having an end most surface and a first sidewall coupled to the first bottom wall at an angle to thereby define a second recessed space. The second housing section can alternatively comprise a contact surface.

The method can further comprise placing a canted coil spring inside a first recessed space.

The method can further comprise attaching said first housing section to said second housing section to form a connector housing having an interior cavity with a housing groove comprising a groove bottom and two sidewalls.

The method wherein the housing groove can be cooperatively defined by the first and second bottom walls attached to one another at their respective endmost surfaces or the endmost surface of the first bottom wall attached to the contact surface.

The method wherein said canted coil spring can be placed in contact with said first housing section after said attaching step.

The method can further comprise placing said connector housing in contact with a seal element and into a header of an implantable medical device.

The method wherein the first housing section can be attached to the second housing section by welding or held together by an encapsulation layer.

It has been found that the elliptical profile of typical canted coil springs may result in rolling of the canted coil spring within grooves and out of optimal position during spring engagement, connection, vibration, or installation, resulting in inconsistent performance, undesirable connection force variations, or improper connector function. A V-bottom groove configuration may be used to address this issue by keeping the canted coil spring centered within the groove and discouraging roll. However, this groove configuration requires additional or more complex fabrication and can increase manufacturing costs. As such, housings formed with one or more stamped housing sections and having a V-bottom can continue to be used with traditional elliptical shaped coils of canted coil springs as these housings are less complex and less costly to manufacture. Alternatively, canted coil springs can be modified for use with flat bottom grooves and address the issue of rolling. These modified shaped canted coil springs can also be used with housings formed with stamped housing sections.

The canted coil springs having a plurality of coils all canted in the same direction along a centerline and applications of the canted coil springs of the present disclosure can advantageously address the rolling issue of a conventional canted coil spring located within grooves, of increased manufacturing costs due to complex groove configurations, regarding a tendency to come out of its groove during operation, vibration or shock, unwanted slipping in rotary applications, and a limited number of electrical contact points by providing a canted coil spring with complex coil shape to improve connector performance by overcoming the mentioned issues, among others.

Aspects of the present disclosure include a canted coil spring with complex coil shape for improving connector performance comprising a continuous plurality of coils and a spring axis through said coils; each coil comprising a coil shape and a cross-sectional axis and canted about said cross-sectional axis; said coil shape can be defined by two generally parallel straight segments with an elliptical segment at each end of the two generally parallel straight segments that joins the straight segments together.

The canted coil spring with complex coil shape for improving connector performance wherein the cross-sectional axis can be generally perpendicular to the generally parallel straight segments.

The canted coil spring with complex coil shape for improving connector performance wherein the cross-sectional axis can be generally parallel to the generally parallel straight segments.

Another feature of the present disclosure is a canted coil spring with complex coil shape for improving connector performance comprising a continuous plurality of coils and a spring axis through said coils; each coil comprising a coil shape and a cross-sectional axis and canted about said cross-sectional axis; said coil shape can be defined by a polygonal geometry.

The canted coil spring with complex coil shape for improving connector performance wherein the cross-sectional axis can be generally parallel to a straight segment of said polygonal geometry of said coil shape.

The canted coil spring with complex coil shape for improving connector performance wherein said polygonal geometry can be a triangle.

The canted coil spring with complex coil shape for improving connector performance wherein said triangle can be an isosceles triangle.

The canted coil spring with complex coil shape for improving connector performance wherein said triangle can be a right triangle.

The canted coil spring with complex coil shape for improving connector performance wherein said polygonal geometry can be a rectangle.

The canted coil spring with complex coil shape for improving connector performance wherein said polygonal geometry can be a parallelogram.

The canted coil spring with complex coil shape for improving connector performance wherein said polygonal geometry can be a pentagon.

The canted coil spring with complex coil shape for improving connector performance wherein said polygonal geometry can be five sided.

Yet further aspects of the present disclosure include a canted coil spring with complex coil shape for improving connector performance comprising a continuous plurality of coils of wire, a spring axis through said coils, and a cross-sectional profile when viewed in the direction of said spring axis; each coil canted about an axis generally perpendicular to said spring axis; said cross-sectional profile can define a star geometry with said wire following a pentagram pattern.

Still further aspects of the present disclosure include a canted coil spring with complex coil shape for improving connector performance comprising a continuous plurality of coils of wire, a spring axis through said coils, and a cross-sectional profile when viewed in the direction of said spring axis; each coil canted about an axis generally perpendicular to said spring axis; said cross-sectional profile can define a multi-loop geometry with said wire following a repeating pattern of distinct and partially overlapping loops to define said multi-loop geometry.

The canted coil spring with complex coil shape for improving connector performance wherein said multi-loop geometry can comprise at least one tear drop shaped loop.

The canted coil spring with complex coil shape for improving connector performance wherein said multi-loop geometry can comprise multiple tear drop shaped loops each comprising a tear drop tip, wherein each tear drop tip generally converges to the same point when viewing the cross-sectional profile.

The canted coil spring with complex coil shape for improving connector performance wherein said multi-loop geometry can comprise at least two overlapping loops; each loop sharing a tangent with at least one other loop when viewing the cross-sectional profile.

Yet an additional aspect of the present disclosure is a canted coil spring with complex coil shape for improving connector performance comprising a continuous plurality of coils of wire, a spring axis through said coils, and a cross-sectional profile when viewed in the direction of said spring axis; each coil canted about an axis generally perpendicular to said spring axis; said cross-sectional profile can be a non-elliptical and non-rectangular shape and can comprise at least an interior loop that is entirely within said cross-sectional profile.

A connector with improved performance can comprise a canted coil spring of any shaped coils described herein.

Methods of making and of using the canted coil springs having complex coil shapes described herein are within the scope of the present disclosure.

A connector with a housing having a multi-piece structure assembled together to form a housing groove with at least one piece forming the housing being made by stamping and cold forming at least part of the shape of the housing groove; and wherein a canted coil spring of any shaped coils described herein is located within the housing groove. The coils can have a dimple for forming two or more contact points or for engaging a convex projecting in a latching connector application.

A still further aspect of the present disclosure includes a connector assembly comprising: connector housing comprising a first housing section attached to a second housing section and having an interior cavity with a housing groove; wherein the first housing section comprises a first bottom wall with an end most surface and a first sidewall coupled to the first bottom wall at an angle; wherein the second housing section comprises a second bottom wall with an end most surface and a second sidewall coupled to the second bottom wall at an angle; wherein the first bottom wall and the second bottom wall define a groove bottom of the housing groove and the first sidewall and the second sidewall define two sidewalls of the housing groove; wherein the endmost surfaces of the first housing section and second housing sections are welded together to form the connector housing having two opening.

The connector assembly wherein the first housing section and the second housing section can be substantially identical.

The connector assembly wherein the two openings can align to receive a pin.

The connector wherein the angle of the first housing section can be a right angle, an acute angle, or an obtuse angle.

The connector assembly can further comprise a canted coil spring located in the housing groove, wherein the canted coil spring can comprise a plurality of coils and wherein each of the plurality of coils comprises a dimple.

The connector assembly wherein the coils with the dimples each can comprise a straight segment.

The connector assembly wherein the angle of the first housing section can be a right angle and the angle of the second housing section can be a right angle. The two angles can produce a groove bottom wall that is generally straight or flat.

The connector assembly can further comprise a canted coil spring located in the housing groove and wherein the canted coil spring can comprise a plurality of coils each with three or more straight segments and defining an angle α and angle β between the three or more straight segments.

The connector assembly wherein a base of each of the plurality of coils has a straight segment for forming a line contact with a bottom surface of the housing groove.

The connector assembly wherein angle α can be equal to angle β, angle α can be greater than angle β, or angle α can be less than angle β.

The connector assembly can further comprise a dimple on a segment of each of the plurality of coils for forming two contact points at each of the plurality of coils.

An additional aspect of the present disclosure is a method of assembling a connector comprising: providing a connector housing comprising at least two housing sections and wherein at least one of the two housing sections has a contoured formed by cold working a die; said housing comprising a housing groove comprising a bottom wall located between two sidewalls; placing a canted coil spring inside the housing groove, said canted coil spring comprising a plurality of coils each with three or more straight segments and defining an angle α and angle β between the three or more straight segments; and wherein a base of each coil forms a line contact with the bottom wall of the housing groove.

The method wherein the connector housing can have two openings and wherein a pin can be inserted through a ring center of the canted coil spring and the two openings of the connector housing.

The method wherein the pin can comprise a convex protrusion and wherein the plurality of coils each can comprise a dimple in contact with the convex protrusion.

The method wherein angle α can be equal to angle β, angle α can be greater than angle β, or angle α can be less than angle β.

The method wherein the plurality of coils each can comprise a dimple and wherein each coil can have two contact points with the pin at the dimple.

The method wherein two of the three straight segments can be side segments and one of the three straight segments can be a bottom segment joining the two side segments, and wherein a curved upper segment can join the two side segments.

The method wherein the curved upper segment can include a dimple.

BRIEF DESCRIPTION OF DRAWINGS

These and other features and advantages of the present devices, systems, and methods will become appreciated as the same becomes better understood with reference to the specification, claims and appended drawings wherein:

FIG. 1 shows one embodiment of a connector assembly, the connector assembly including a canted coil spring, a connector housing (or simply housing), and a pin engaging the connector housing, the connector housing including a stamped housing section joined to another stamped housing section, the joined stamped housing sections including a bottom wall and a sidewall joined to the bottom wall.

FIG. 2 is similar to FIG. 1, except that the pin has a groove therein for receiving a part of the spring, such as in a latching where the pin can subsequent separate from the housing or a locking application where the pin cannot separate unless the spring is deformed from its initial state.

FIG. 3 shows another embodiment of a connector assembly, the connector assembly including a canted coil spring, a connector housing, and a pin engaging with the connector housing, the connector housing including a stamped housing section joined to a surface, the stamped housing section including a bottom wall and a sidewall joined to the bottom wall. The surface can be part of a housing body that can have a variety of shapes, including a flat plate with a bore or opening; a flange with a bore or opening, or a block with a bore or opening.

FIG. 4 is similar to FIG. 3, but shown with a lead connected through the surface of the housing body to reach the stamped housing section.

FIG. 5 shows yet another embodiment of a connector assembly, the connector assembly including a pin, a canted coil spring, and a connector housing, the connector housing including a stamped housing section joined to another stamped housing section, the stamped housing sections including a bottom wall and a sidewall joined together at an angle.

FIG. 6 is similar to FIG. 5, except that the pin has a groove therein for receiving a part of the spring.

FIG. 7 shows still yet another embodiment of a connector assembly, the connector assembly including a pin, a canted coil spring, and a connector housing, the connector housing including a stamped housing section joined to a surface, the stamped housing section including a bottom wall and a sidewall joined to the surface at an angle.

FIG. 8 is similar to FIG. 7, except that the pin has a groove therein for receiving a part of the spring.

FIG. 9 is similar to FIG. 7 but shown without a pin and with a lead connected through the surface to the housing section.

FIG. 10 shows an alternative embodiment of a connector assembly, the connector assembly including a connector housing and a canted coil spring mounted to an exterior of the connector housing and an external housing having a bore receiving the connector housing with the spring, the connector housing including a stamped housing section joined to another stamped housing section, the stamped housing section including a bottom wall and a sidewall joined to one another.

FIG. 11 is similar to FIG. 10, except that the bore of the external housing has a groove therein for receiving a part of the canted coil spring.

FIG. 12 shows another alternative embodiment of a connector assembly, the connector assembly including a connector housing and a canted coil spring mounted to an exterior of the connector housing for use with an external housing having a bore receiving the connector housing and spring, the connector housing including a stamped housing section joined to a surface, the stamped housing section including a bottom wall and a sidewall.

FIG. 13 is similar to FIG. 12, but shown with a lead connected through the surface to the housing section.

FIG. 14 shows yet another alternative embodiment of a connector assembly, the connector assembly including a connector housing and a canted coil spring mounted to an exterior of the connector housing and an external housing having a bore receiving the connector housing and spring, the connector housing including a stamped housing section joined to another stamped housing section, the stamped housing section including a bottom wall and a sidewall joined to one another.

FIG. 15 is similar to FIG. 14, except that the external housing bore has a groove therein for receiving a part of the spring.

FIG. 16 shows still yet another alternative embodiment of a connector assembly, the connector assembly including a connector housing and a canted coil spring mounted to an exterior of the connector housing and an external housing having a bore receiving the connector housing and spring, the connector housing including a stamped housing section joined to a surface, the stamped housing section including a bottom wall and a sidewall joined.

FIG. 17 is similar to FIG. 16, except that the external housing bore has a groove therein for receiving a part of the spring.

FIG. 18 is similar to FIG. 16, but shown with a lead connected through the surface to the housing section.

FIGS. 19A and 19B show cross-sectional views of two differently arranged or orientation of a canted coil spring with a coil shape defined by two generally parallel straight segments with an elliptical segment at each end that joins the two generally parallel straight segments together installed in a rectangular groove.

FIGS. 20A, 20B, and 20C show cross-sectional views of three canted coil springs of different coil geometries, such as different polygonal geometries, adapted to the geometry of the groove they are installed in.

FIGS. 23A and 23B show cross-sectional views of two canted coil springs with pentagonal geometries where angle α is not equal to angle β.

FIGS. 23C and 23D show cross-sectional views of two canted coil springs with right trapezoidal geometries where angle α is not equal to angle β.

FIGS. 23E and 23F show cross-sectional views of two canted coil springs with pentagonal geometries where the coil height and the wire thickness used to form the coils are increased, respectively.

FIG. 24 shows a cross-sectional view of three canted coil springs, said cross-sectional view showing the coils each being a non-elliptical and non-rectangular shape and comprising one interior loop that is entirely within said coil contour and positioned in a housing with three correspondingly sized rectangular grooves and a piston with three corresponding convex protrusions contacting dimples formed by the interior loops.

FIG. 30 shows a cross-sectional view of a canted coil spring having a plurality of coils located in a housing and usable with a pin and wherein the housing is multi-piece and wherein at least one piece is formed by stamping and having a curvature or bend formed by cold working a blank.

FIG. 31 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 32 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 33 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 34 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 35 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 36 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 37 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 38 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 39 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 40 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 41 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 42 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 43 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 44 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 45 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 46 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 47 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 48 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 49 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 50 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 51 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 52 shows a cross-sectional view of another canted coil spring having a plurality of coils located in a housing and usable with a pin and wherein the housing is multi-piece and wherein at least one piece is formed by stamping and having a curvature or bend formed by cold working a blank.

FIG. 53 shows a cross-sectional view of another canted coil spring having a plurality of coils located in a housing and usable with an exterior housing having a bore and wherein the housing is multi-piece and wherein at least one piece is formed by stamping and having a curvature or bend formed by cold working a blank.

FIG. 54 shows a cross-sectional view of another canted coil spring having a plurality of coils located in a housing and usable with an exterior housing having a bore and wherein the housing is multi-piece and wherein at least one piece is formed by stamping and having a curvature or bend formed by cold working a blank.

FIG. 55 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 56 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 57 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 58 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 59 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 60 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 61 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 62 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 63 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 64 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 65 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 66 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 67 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 68 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

FIG. 69 shows a cross-sectional view of another canted coil spring having a plurality of coils located in a housing and usable with a pin and wherein the housing is multi-piece and wherein at least one piece is formed by stamping and having a curvature or bend formed by cold working a blank and the coil having a dimple.

DETAILED DESCRIPTION

Figures 21A, 21B:
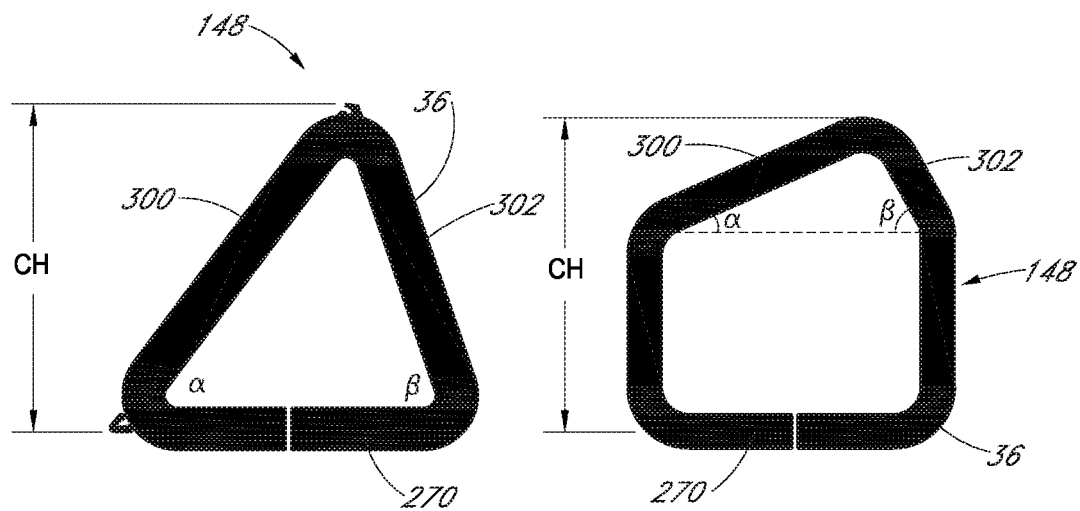
FIGS. 21A and 21B show cross-sectional views of two types of canted coil spring geometries where angle α can determine insertion force and angle β can determine removal force when used in a mechanical connector.

The detailed description set forth below in connection with the appended drawings is intended as a description of the presently preferred embodiments of stamped housing sections and canted coil springs for use in various connector applications provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

FIGS. 1-9 are cross-sectional views of multiple embodiments of a first connector assembly 10, the connector assembly 10 including a connector housing 130 having a bore 106 with an inner groove 140 located therein and a spring 148 received in the inner groove 140. The connector assembly 10 is configured, such as sized and shaped, to receive or engage a lead or pin 40, such as by gripping the pin with the spring 148. Pins disclosed herein are solid unless indicated otherwise and have a solid end wall at the insertion end of the pin for inserting into a bore of a housing. FIGS. 10-18 are cross-sectional views of multiple embodiments of a second connector assembly 20, the second connector assembly 20 including a connector housing 230 having an outer groove 240 and a spring 148 received in the outer groove 240. The connector assembly 20 is configured, such as sized and shaped, to project into a bore 80 of an external housing 85. The canted coil springs disclosed herein have a number of interconnected coils all canted in the same direction of a coil centerline. Each canted coil spring has two ends connected to form an annular or garter shaped spring structure, especially where shown or discussed in connection with a connector having a pin or piston. However, the canted springs may be practiced as a spring length wherein two ends of each spring length are not connected. As is well known in the art, canted coil springs can be coiled so that the coils deflect along a radial direction relative to the coil centerline. A standard helical spring can only compress or expand along a comparable coil centerline but the coils cannot cant or deflect radially of the centerline.

For the connector assemblies (10, 20) and connector assembly components disclosed herein, it is understood that where a feature is shown but not expressly described and is otherwise the same or similar to the feature or features described elsewhere, such as above with reference to FIGS. 1-18, the disclosed part or parts shown in all the drawing figures but not expressly described because of redundancy and because knowledge is built on a foundation laid by earlier disclosures may nonetheless be understood to be described or taught by the same or similar features expressly set forth in the text for the embodiments in which the feature or features are described. Said differently, subsequent disclosures of the present application are built upon the foundation of earlier disclosures unless the context indicates otherwise. The disclosure is therefore understood to teach a person of ordinary skill in the art the disclosed embodiments and the features of the disclosed embodiments without having to repeat similar components and features in all embodiments since a skilled artisan would not disregard similar structural features having just read about them in several preceding paragraphs nor ignore knowledge gained from earlier descriptions set forth in the same specification. As such, the same or similar features shown in the following connector assemblies incorporate the teachings of earlier embodiments unless the context indicates otherwise. Therefore, it is contemplated that later disclosed embodiments enjoy the benefit of earlier expressly described embodiments, such as features and structures of earlier described embodiments, unless the context indicates otherwise.

With reference to FIGS. 1-2 and 5-6, one embodiment of a connector housing 130 includes a housing section 100 coupled to another housing section 100. The two housing sections 100 can be substantially identical to one another or can be different. With reference to FIGS. 3-4 and 7-9, another embodiment of a connector housing 130 includes a housing section 100 coupled to a surface 60 of a body 65, which can be a plate, a flange, or a shoulder of a base or a frame. The surface 60, which can be referred to as a contact surface 60, of the body may be viewed as a second housing section attached to the first housing section 100, which has a stamped curvature or a stamped groove structure.

The housing section 100 of FIGS. 1-9 each has an outer perimeter 104 and a bore 106. Each housing section 100 can be configured to cooperate with a surface 60 or another housing section 100 to form a connector housing 130 having a housing groove 140 for receiving a spring 148, which can be a radial canted coil spring or an axial canted coil spring with a plurality of interconnected coils all canted in a same general direction. The canted coil spring used with the housing groove 140 of the connector housing 130 can have conventional elliptical or oval shaped coils or complex coil shapes, such as shown with reference to FIGS. 19A-B, 20A-C, 21A-B, 22, 23A-23F, 24, 26A-26D, 28, 29A-B, and 30-69. In one example, the bore 106 of a housing section 100 is generally round for receiving a round pin 40 or a shaft, rod, or piston. In other examples, the bore 106 can embody other shapes, such as square or oval for receiving a similarly shaped pin. The outer perimeter 104 can also have the same or different shape as the shape of the bore 106. For example, the bore 106 can be round while the outer perimeter 104 can be square, oval, or rectangular. In the illustrated embodiment, the outer perimeter 104 and the bore 106 both have a round shape.

With continued reference to FIGS. 1-9, the housing section 100 can be made using a coining process, which is a cold working process similar to forging, except the latter usually takes place at elevated temperatures. A die or multiple dies may be used in a coining process to first cut a blank and then shaping the blank into a refined shape, which can optionally further be machined or laser treated to further modify the final shapes and tolerances. The die or dies used to shape the blank may have different shapes and contours for forming a different shaped housing section 100. Generally speaking, the shaped housing section 100 can be described as a negative image of the die or dies. A great deal of force is used to plastically deform a blank or work piece. In one example, a hydraulic actuated press is used to supply the working pressure. In other examples, a gear driven press or a mechanical press may be used to supply the working pressure. Coining is similar to stamping with the difference primarily being the working force or pressure. Unless the context indicates otherwise, coining and stamping for purposes of the present disclosure are used synonymously.

Blank materials usable as the starting point for forming the disclosed housing sections 100 can be made from any number of conductive metals. Examples of metals that are capable of conducting current include steel, stainless steel, copper, and gold. Additionally, stainless steel type 316L, MP35N, platinum-iridium, titanium, and others can be used. Multi-metallic metal may also be used by coating a base metal layer with a relatively higher conductive material or layer. For example, the base material may be copper, which is relatively soft metal, and the stamped copper base layer is subsequently overlaid with a harder material, such as stainless steel. Alternatively, the material can be a conventional medically implantable grade material with noble metal coatings, such as platinum over stainless steel. By coating a non-noble metal element with a noble metal, the more desirable conductive and corrosion resistant properties of the noble metal are married with the significantly lower cost of non-noble metals such as high-strength nickel alloys and stainless steel. Thus, the stamped housing section 100 can be made from a single metal material or a multi-layer metal material with the latter having a base metal layer and one or more cladding or plating over-layers. For certain connector applications, plastic injection molding can also be employed to form the stamped housing and then providing a path through the plastic housing to terminate an electrical lead to the canted coil spring. For pure mechanical applications without current or signal carrying capability, two injection molded housing sections can be joined with a canted coil spring located in between to form a connector housing 100.

As shown, the housing section 100 comprises a bottom wall 110 and a sidewall 114 coupled to the bottom wall 110. In the present embodiments, the sidewall 114 of each housing section 100 extends inwardly towards the bore 106. A free end of the bottom wall 110 is configured to mate to another surface, such as to another free end of a joining housing section 100, and functions as a joining surface 112. The free end can be a terminal end of the bottom wall 110 and not a flange or some extension extending from the bottom wall and mate to a corresponding extension. The two free ends preferably of the two housing sections dos not include mechanical inter-engagement. The two joining surfaces 112 of two housing sections, which can be endmost surfaces of the bottom walls 110, are secured together, such as by laser welding or spot welding, to form a housing or connector groove 140. In some examples, the endmost surfaces 112 of two joining housing sections 100 face one another or angled from one another. When facing one another, the angle between them is zero and is also known as butt-joint. When angled from one another, the angle between the two surfaces can be less than 180 degrees.

The bottom wall 110 and the sidewall 114 can be flat, have a curved surface, can be angled relative to one another, or are irregularly shaped surfaces. In one example, the bottom wall 110 and the sidewall 114 have a generally flat or planar section. The bottom wall 110 forms an angle with the sidewall 114. In some embodiments, the angle is about 90 degrees (FIGS. 1-4). In other embodiments, the angle is an obtuse angle (FIGS. 5-9). In still other embodiments, the angle between the sidewall 114 and the bottom wall 110 of at least one of two housing sections is acute. The bottom wall 110 and the sidewall 114 cooperatively define a recessed space 120. Two recessed spaces 120 from two housing sections 100 can be called recessed spaces. The recessed space 120 is configured to accommodate a spring 148, as further discussed below. Each housing section 100 can contact another housing section 100 when stacking a plurality of housing sections 100 in a stack (not shown) with all housing sections 100 facing the same direction, such as for packaging, storing, and/or shipping.

Two housing sections 100 can be brought together and joined to form a connector housing 130. The recessed spaces 120 cooperatively form an internal housing groove 140, which may sometimes be referred to as a groove, a spring groove, a connector groove or a channel for accommodating a canted coil spring. In other embodiments, a single housing section 100 is configured to contact a surface 60 of a support body 65 instead of another stamped housing section. The free end of the single section 100 can attach, such as weld to, the surface without incorporating an extension or a flange that extends from the bottom surface. The body 65 with the surface 60 is considered as a housing section but can be made from other than coining or stamping. For example, the support body 65 may be stamped to create a cutout from a stock material. Alternatively, the support body 65 may be machined, cast, or forged from a stock material. In any event, the support body 65 is a housing section in that it is joined to another housing section to form a connector housing 130 having a spring groove 140. The connector housing 130 can be conductive when selecting appropriate conductive metallic material or a combination of materials for the housing sections 100 and can be referred to as a conductive contact element, such as when used in combination with an in-line header connector, as further discussed below, or as an electrical connector when used with a pin or rod to transmit electrical signals or power between two electronic sources or components, such as between a circuit board and a power supply.

In one example, a blank for forming a housing section, such as the housing sections 100 disclosed in the various embodiments, has a generally constant thickness, which can be sized or selected depending on the material hardness and the type of connector application to be used, such as for heavy duty high insertion and/or removal force applications, for a mechanical connector, for an electrical connector, etc. In other examples, the thickness can vary along the blank to allow for bending and shaping the contour of the housing section 100. By forming the housing section 100 using a stamping process rather than machining the housing from a metal block, consistent housing dimensions and thinner sections can be obtained, which can reduce the overall length or size of a completed product, such as the overall size of an in-line connector stack, and reduce manufacturing costs. A stamped housing section can also be formed relatively quicker than forming the same housing by machining. The joining surface 112 can be machined after stamping to improve attachment, such as to facilitate welding.

With reference to FIGS. 1, 2, 5, and 6, the connector housing 130 can be formed by joining two housing sections 100 together. The two housing sections 100 can be joined by first placing them in opposing contact so that the outer perimeters 104 lined up, such that the joining surfaces 112 abut against each other or are in adjacent contact. The two housing sections 100 can then be simply welded together, such as with spot welds, laser welds, or continuous welds, to form the connector housing 130. An outer encapsulation sleeve or layer can also be used to capture and hold the two housing sections 100 together instead of or in addition to welding. The encapsulation sleeve is disclosed in U.S. Publication No. 2014/0079476, the contents of which are expressly incorporated herein by reference to teach use of encapsulation sleeves together with connector housings and canted coil springs disclosed herein. The connector housing 130 can also be used as is and be connected to a wire or cable, which can be connected to an electrical source or component. The connector housing 130 can also be used as is with a pin or a shaft to function as a mechanical connector, which can be a holding connector, a latching connector, or a locking connector in which the pin cannot move in the opposite direction to disconnect from the connector housing 130 without destroying the connector, such as destroying the spring.

As shown, the connector housing 130 can be created by two separately formed housing sections 100 that are attached together. As shown, a housing groove 140 can be formed by the two joined housing sections 100. Said differently, the housing groove 140 can be cooperatively defined by joining two stamped housing sections 100 together. In an example, two end surfaces of two bottom walls 110 are placed side-by-side and then welded to from a connector housing 130. In some embodiments, the two connected housing sections 100 are substantially the same. That is, the housing groove 140 is formed by joining two identical housing sections 100 together. In other embodiments, the two connected housing sections 100 are different. That is, two non-symmetrical housing sections can join to form a housing groove 140 that is non-symmetrical about the joined interface. The housing groove, spring groove, or channel 140 can be generally U-shaped (see FIGS. 1-4) in which the angle of the bottom wall 110 with respect to each of the two sidewalls 114 is substantially perpendicular. In other embodiments, by modifying the angle of the bottom wall 110 with respect to the sidewall 114 of one or both housing sections 100, the shape of the groove 140 can be altered. For example, the bottom wall 110 can form an obtuse angle with respect to the sidewall 114 to form a V shape (see FIGS. 5-9) when two housing sections are joined. The connector housing 130 can also embody a V-shaped groove without any sidewall 114. In yet other examples, the V-groove can have a flat bottom surface therebetween, i.e., a subtended bottom surface located between two tapered surfaces, which may or may not include sidewalls. Thus, the connector housing 130 can be viewed as having a common bore 106 and a housing groove 140 formed by coining all or part of at least one of the housing sections and then joining them together via welding. The housing sections 100 can be joined by aligning two ends of two bottom walls 110 adjacent one another and then welding the seam or parting line therebetween.

Again, the housing groove 140 is shown with a groove surface formed by the two bottom walls 110 and the two sidewalls 114 of the two housing sections. In some examples, the groove is V-shaped with two slanted surfaces joined together and without any sidewall. In the embodiments shown, such as FIGS. 1 and 2, the groove 140 has a parting line or seam generally at the middle of the housing groove 140. In yet other examples, if the housing sections 100 are not symmetrical, the parting line of the housing groove 140 can be offset from center, such as shown in FIGS. 3 and 4. As shown, the two housing sections 100 are symmetrical about the interface 136. In other words, the two housing sections 100 can be understood to be formed from stamping and be symmetrical about the interface 136, which can also be called a seam or a parting line. Said differently, a connector housing 130 can be provided by joining two symmetrical stamped housing sections 100 about an interface 136 to form the housing groove 140. More particularly, the two housing sections of the various embodiments are joined at the joining surfaces 112, which are endmost surfaces of the respective bottom walls 110. The length of the bottom wall 110 can be adjusted to determine the width of the housing groove 160 or be dependent on the type and/or size of the spring 148 to be accommodated in the groove. Similarly, the length of the sidewall 114 of the housing section 100 and angle between the sidewall 114 and the bottom wall 110 can be adjusted to determine the depth of the housing groove 140. The groove of the various embodiments is sized so that when used with a canted coil spring and the spring receives a pin or shaft, with or without a pin groove, the spring touches the bottom of the connector housing groove. In other examples, the pin has a groove and when inserted through the spring, the spring is spaced from the bottom of the housing groove. The spring can contact the two sidewalls of the groove, contact only one of the two sidewalls, or be spaced from the two sidewalls of the groove. The spring can also simultaneously contact two tapered surfaces of the housing groove when the pin is inserted into the housing bore. As previously alluded to, the term stamped housing section 100 does not preclude some machining, such as to fine tune certain geometries of the housing sections 100 to fine tune the completed connector housing 130. The connector housing 130 can also be machined to certain dimensions.

With reference now to FIGS. 3, 4, and 7-9, a single housing section 100 can be coupled to, mate, or abut against a surface 60 of a body 65 to form a connector housing 130. The surface 60 can be flat, arcuate, or irregular. In the illustrated embodiment, the surface 60 is flat. The body 65 can embody any number of structures, such as a flange, a washer, a frame, or a plate. The body 65 may be referred to as a housing body for joining to a housing section 100, the latter being a stamped component. The housing section 100 and the housing body 65 together define a housing groove. In the example shown, the housing body 65 defines at least part of a housing groove 140. The stamped housing section 100 also defines at least part of the housing groove 140.

The outer perimeter 104 of the housing section 100 can be situated close to the outer perimeter 64 of the housing body 65, such as radially aligned along respective outer perimeters, or recessed from the outer perimeter 64 of the housing body 65. The inner perimeter 66 of the body 65 can be substantially similar to the size or diameter of the bore 106 of the housing section 100. The connector housing 130 there has two end openings and a bore 106 therebetween and wherein the two end openings have generally the same diameter or dimension. The housing groove 140 is cooperatively defined, at least in part, by the sidewall 114 of the housing section 100, the bottom wall 110, and the surface 60 of the body 65. The width of the bottom wall 110 can be adjusted to determine the width of the housing groove 140, which can depend on the type and/or size of the spring 148 to be accommodated. Similarly, the length of the sidewall 114 of the housing section 100 can be adjusted to determine the depth of the housing groove 140. The bottom wall 110 of the housing section 100 can be perpendicular or form an angle with the surface 60 of the body 65. The sidewall 114 of the housing section 100 can be parallel or form an angle with the surface 60 of the body 65. In the embodiment of FIGS. 3, 4, and 7-9, the bottom wall 110 of the connector housing 130 can be formed entirely from or by the stamped housing 100.

With reference to FIGS. 4 and 9, the body 65 can have an opening, channel, path, or a bore 55 through the surface 60 to allow a conductive lead 70 to pass through the body 65 to electrically connect to the housing section 100, the canted coil spring 148 or both. The conductive lead 70 can be electrically secured to the housing section 100, such as by welding an end of the conductive lead 70 to a surface of the housing section 100. The conductive lead 70 can alternatively be pressed fit through the bore 55. The housing body 65 is also made from an electrically conductive material.

As shown, a canted coil spring 148 is located in the housing groove 140 of the connector housing 130, i.e., the canted coil spring 148 is housing mounted. The canted coil spring 148 can be an axial canted coil spring or a radial canted coil spring and the spring 148 can comprise a plurality of coils 36 all canted in the same general direction with each coil 36 comprising a major axis and a minor axis, such as being elliptical in shape with a major axis and a minor axis, which is shorter than the major axis. This canted feature is contrasted with normal expansion or compression springs, which are coiled with coils having opposing tapers so that the individual coils cannot compress in the radial direction due to the opposing structures. In other examples, the spring can be a garter spring, a cantilever spring, or a ribbon spring. Exemplary canted coil springs are disclosed in U.S. Pat. Nos. 4,655,462; 4,826,144; and 4,876,781, the contents of which are expressly incorporated herein by reference. The canted coil springs 148 can have coils of other different shapes, other than elliptical, as shown in FIGS. 19A-B, 20A-C, 21A-B, 22, 23A-23F, 24, 26A-26D, 28, 29A-B, and 30-69.

The canted coil springs 148 disclosed herein can be made from a conductive metal and can be plated or cladded with one or more outer layers over a base metallic layer. As used herein, conductive metal is understood to mean any metal capable of conducting current, such as steel, stainless steel, copper, and gold. In certain embodiments, a preferred conductive metal, such as copper, copper alloy, or a preferred combination, such as copper with silver or other noble metal cladding, can be used. For high temperature applications, a soft base metal can be used with a high tensile strength outer layer, such as a copper core with a stainless steel outer layer. In another example, the combination can be practiced in the reverse, i.e., with the high tensile strength material as the base core material and the high conductive property material, such as copper, as the cladding outer layer. In still yet other examples, the high tensile strength property material can include heat treated carbon steel, INCONEL® alloys, and HASTELLOY® alloys. INCONEL alloys are understood to include a family of nickel-chromium-based super alloys. HASTELLOY are understood to include a family of nickel based super alloys that include varying percentages of elements such as molybdenum, chromium, cobalt, iron, manganese, etc. In an example, the second conductive clad layer having high conductivity can include copper, copper alloy, aluminum, aluminum alloy, gold, gold alloy, silver, silver alloy, brass, or brass alloy. The combination with a high tensile strength base material and a conductive cladding material is configured to offer high conductivity as well as retain high tensile and high modulus properties at elevated temperatures. The high conductivity layer is preferably positioned on the side of the spring that contacts or faces a pin 40. However, in another embodiment, the high tensile strength material can contact or face the pin 40.

With reference again to the FIGS. 1-9, the inner diameter 150 of the spring 148 is smaller than the diameter of the bore 106 so that the spring projects outwardly of the groove and towards the centerline or lengthwise axis of the pin. The inner diameter 150 of the canted coil spring 148 is also smaller than the nominal diameter of the pin 40. Thus, when the pin 40 is inserted in through the bore 106 the pin 40 and the center of the canted coil spring 148, the pin makes contact with the spring 148 and the spring 148 is biased against the housing groove 140 and the pin 40 to form a mechanical connector and optionally with current or electric carrying capability, if connected to electrical sources. The pin 40 can have an exterior groove 44 (shown in FIGS. 2, 6, and 8), such as for a latching or a locking application, or can be without a groove (shown in FIGS. 1, 5, and 7), such as for a holding application. The housing groove 140 can have a width that is narrower than the coil major axis so that the major axes of the coils, which are longer than the width, are rotated and contacting and being constrained by the groove sidewalls, when the spring 148 is positioned in the housing groove 140. The width of the housing groove 140 can also be wider than the coil major axis and/or the coil minor axis so that the coils do not touch the sidewalls of the housing groove 140 when placed therein. Still alternatively, the groove depth can be such that the spring does not touch the bottom surface of the housing groove 140 when the pin 40 is not present and wherein when the pin 40 is inserted, the pin 40 pushes on the spring so that the outer diameter 155 of the coils contact the bottom surface of the housing groove 140. This feature allows for low insertion force when inserting the pin into the spring center and into the bore of the housing 130

The connector housing 130 and pin 40 combination, using the present disclosed stamped housing sections 100, is capable of being used in numerous applications and industries as mechanical connectors and optionally with electrical carrying capabilities, i.e., as electrical connectors. For example, the connector housing 130 with at least one stamped housing section 100 and pin 40 combination can be used in aerospace, automotive, consumer electronics, and oil and gas applications to secure a first object to a second object or to conduct electricity, such as current or signals, between two different sources or nodes.

During assembly, the spring 148 can be placed in the recessed space 120 of a first housing section 100 and then a second housing section 100 is attached to the first housing section 100. Alternatively, the spring 148 can be placed in the recessed space 120 of the first housing section 100 and then together mounted to the surface 60 of a housing body 65. This allows the spring 148 to be installed within the connector housing 130 with minimal deflection and stress to the spring 148, which in turn reduces the possibility of mis-orientation of the spring contact within the housing groove 140. The installation of the spring 148 when the housing section 100 is already joined to the other housing section 100 would require deflecting the spring 148 a significant amount to fit the spring 148 through the housing bore diameter, and then once through the bore diameter the spring 148 can expand into the housing groove 140. However, this process can lead to the spring 148 being tilted or mis-oriented within the groove upon expanding, thus possibly resulting in a high force insertion or removal of the pin 40 in through the bore 106 of the one-piece connector housing 130, such as by having the pin 40 contacting the spring 148 closer to the major axis of the spring coils. However, it is contemplated that the presently disclosed connector housing can be used with a canted coil spring after two housing sections are joined. The groove 140 is sized and shaped to accommodate a canted coil spring 148, which is shown as a radial canted coil spring with an axial canted coil spring contemplated, such as shown in FIG. 9. While only two coils 36 of the canted coil spring 148 are shown, the canted coil spring 148 is understood to include a plurality of interconnected coils all canted in the same direction. Furthermore, it is understood that the spring will only deflect in the canting direction along one of the two axes but not both. In some examples, coils can deflect along two different axes, as disclosed in co-pending U.S. Publication No. 2015/0240900, filed Feb. 24, 2015, the contents of which are expressly incorporated herein by reference. The canted coil springs disclosed in the co-pending publication No. 2015/0240900 can deflect along two different axes. These springs are usable with the connector housings of the present application, which has at least one housing section that has been stamped.

As discussed elsewhere herein, the pin 40 may have an external groove to latch or lock the pin 40 to the housing 130, such as by capturing the spring 148 in between the housing groove and the pin groove, or without an external groove to hold the pin 40 to the housing, such as by using spring bias force to push against the flat exterior surface of the pin 40 to hold the pin 40 using friction and biasing forces. The pin 40 preferably includes a tapered pin insertion end 46 to facilitate inserting the pin into the bore of the connector housing and through the inside diameter of the spring. Exemplary use of holding, latching, and locking connectors but without the unique housing connectors and grooves utilizing stamped connector parts are disclosed in U.S. Pat. Nos. 4,678,210; 5,082,390; 5,411,348; and 8,297,662, the contents of which are expressly incorporated herein by reference. Any of the various pins disclosed in these patents may be used with the connector housings of the present disclosure, which has at least one housing section having a stamped surface. The pin 40 is shown with a tapered insertion end 46 and optionally with a groove 44. The pin 40 can vary in length and is solid throughout with a hollow core contemplated. The insertion end has a planar end surface but can include an opening of a hollow core is incorporated with the pin 40. In the particular embodiment shown, the groove 44 has a bottom wall 42 and two sidewalls 48a, 48b, which can be substantially parallel to each other. In other examples, the wall surfaces 48a, 48b of the pin groove 44 can be tapered and converge to the bottom wall 42 or to a point (i.e., no bottom wall, V-shaped). In still other examples, the bottom wall 42 can have a single taper relative to the other sidewall 48a, 48b. In yet other examples, one sidewall 48a, can be vertical while the other sidewall 48b is slanted or tapered or vice versa. The pin 40 can connect to the housing 130 and be connectable to other components. For example, the pin 40 can be connected to a first object and the connector housing 130 to a second object for securing the first object to the second object via the connector assembly. For an electrical application, current or signals can pass between the first object and the second object.

With reference now to FIGS. 10-11 and 14-15, multiple embodiments of a connector housing 230 of a second connector assembly 20 includes a housing section 200 coupled to another housing section 200. The two housing sections 200 can be substantially identical or be different. FIGS. 12-13 and 16-18 show another embodiment of a connector housing 230 that includes a first housing section 200 coupled to a surface 60 of a housing body 65. The connector housings have externally mounted springs, externally relative to a centerline.

With reference to FIGS. 10-18, cross sectional views of multiple embodiments of a connector housing 230 comprising of a housing section 200 are shown having an outer perimeter 204 and a bore 206. Each housing section 200 can be configured to cooperate with a surface 60 or another housing section 200 to form a connector housing 230 having a housing groove 240 for receiving a spring 148. In one example, the outer perimeter 204 of the housing section 200 is generally round for fitting into a bore 80 of an external housing 85, which can be a sleeve, a tube, or a cylinder for receiving the connector housing 230. In other examples, the outer perimeter 204 can embody other shapes, such as square or oval for projecting into a similarly shaped housing bore 80 of the external housing 85. The outer perimeter 204 can also have the same or different shape as the shape of the bore 206 of the connector housing 230. For example, the bore 206 can be round while the outer perimeter 204 can be square. In the illustrated embodiment, the outer perimeter 204 and the bore 206 both have a round shape.

With reference to FIGS. 10-18, the housing section 200 can be made using a coining or stamping process, as discussed above.

As shown, the housing sections 200 each comprises a bottom wall 210 and a sidewall 214 coupled, joined, or extended from the bottom wall 210. The sidewalls 214 of the housing sections 200 extend outwardly, away from the central bore 206, to form external grooves 240. A free end of each bottom wall 210 acts as a joining surface 212 for joining to another joining surface or a planar or mating surface of an adjacent housing section 200. The joining surface 212 can embody as an end-most surface of the bottom wall 210 of each housing section 200. The joining surface does not have to incorporate any other surface extending from the bottom wall, such as a flange. The bottom wall 210 and the sidewall 214 can be flat or have a curved surface or irregularly shaped. In one example, the bottom wall 210 and the sidewall 214 have a generally flat or planar section. The bottom wall 210 forms an angle with the sidewall 214. In some embodiments, the angle is about 90 degrees (FIGS. 10-13). In other embodiments, the angle is an obtuse angle (FIGS. 14-18). In yet other examples, the angle between the sidewall 214 and the bottom wall 210 of at least one of two housing sections is acute. The bottom wall 210 and the sidewall 214 cooperatively define a recessed space 220. Two recessed spaces 220 define a groove and configured to accommodate a spring 148, as further discussed below. The housing section 200 can contact another housing section 200 when stacking a plurality of housing sections 200 in a stack (not shown) with all housing sections 200 facing the same direction, such as for packaging or shipping.

Two housing sections 200 can be brought together to form a connector housing 230. For example, tack welds or a continuous weld may be made to a parting line or seam between two housing sections to form a connector housing. The recessed spaces 220 of the two housing sections 200 cooperate to form an external housing groove 240 for accommodating a canted coil spring 148 in an external groove of the connector housing 230. In other embodiments, a single housing section 200 is configured to contact a surface 60 instead of another housing section 200 and the two form an external groove. The connector housing 230 can be conductive when selecting an appropriate conductive metallic material or a combination of materials for the housing sections 200, and can be referred to as a conductive contact element, such as when used in combination with an in-line header connector, as further discussed below, or as an electrical connector for electrically coupling two electrical components.

In one example, a blank for forming the housing section 200 has a generally constant thickness, which can be sized or selected depending on the material hardness and the type of connector application to be used, such as for heavy duty high insertion and/or removal force applications, for a mechanical connector, for an electrical connector, etc. In other examples, the thickness of the blank can vary to allow for bending and shaping the contour of the housing section 200. By forming the housing section 200 using a stamping process rather than machining the housing from a metal block, consistent housing dimensions and thinner sections can be obtained, which can reduce the overall length or size of a completed product, such as the overall size of an in-line connector stack, and reduce manufacturing costs. The joining surface 212 can be machined after stamping to improve attachment.

With reference to FIGS. 10, 11, 14, and 15, the connector housing 230 can be formed by joining two housing sections 200 together. The two housing sections 200 can be joined by first placing them in opposing contact or next to one another with the outer perimeters 204 lined up, such that the joining surfaces 212 abut against each other or near one another. The two housing sections 200 can then be welded together, such as with spot welds, laser welds, or continuous welds, to form the connector housing 230. An outer encapsulation sleeve or layer can also be used to capture and hold the two housing sections 200 together instead of or in addition to welding. The connector housing 230 can also be used as is as a connector when placed inside the bore 80 of an external housing 85.

As shown, the connector housing 230 can be created by two separately formed housing sections 200 that are attached together, such as along their respective joining surfaces. At least one of the two housing sections 200 is made form or has a stamped section that has been formed or rolled with a die. As shown, a housing groove 240, such as an external housing groove, is formed by the two joined housing sections 200. Said differently, the housing groove 240 can be cooperatively defined by joining two stamped housing sections 200 together. The external groove 240 can be formed by extending a sidewall from a bottom wall in a radially outward direction, away from a centerline line or bore, and joining two bottom walls of two housing sections together. In some embodiments, the two connected housing sections 200 are substantially the same. That is, the housing groove 240 can be formed by joining two identical housing sections 200 together. In other embodiments, the two connected housing sections 200 are different or having different shapes. That is, a non-symmetrical housing groove 240 can be formed from two different shaped housing sections 200 joined together to form the housing groove 240. The housing groove 240 can be generally U-shaped (as shown in FIGS. 10-13). In other embodiments, by modifying the angle of the bottom wall 210 with respect to the sidewall 214, the shape of the groove 240 can be altered. For example, the depth wall 210 can form an obtuse angle with respect to the sidewall 214 to form a V shape (as shown in FIGS. 14-18). In still yet other examples, two housing sections 200 for forming the connector housing 230 may not be identical and can have two different shaped housing sections 200 to form a non-symmetrical housing groove relative to the interface defined by the intersection of the two joining surfaces 212. Thus, the connector housing 230 can be viewed as having a common bore 206 and a housing groove 240 formed without any machining. In another example, only one of the two housing sections is made from a stamped housing section and coined with a housing bottom and a sidewall while the other section can be machined.

As shown, the housing groove 240 has a bottom surface formed by two bottom walls 210 and two sidewalls 214. In the embodiment shown, the bottom surface has a parting line or seam 236 generally at the middle of the housing groove 240. In yet other examples, if the housing sections 200 are not symmetrical, the parting line 236 of the housing groove 240 can be offset from center. As shown, the two housing sections 200 are symmetrical about the interface 236. In other words, the two housing sections 200 can be understood to be formed from stamping and be symmetrical about the interface 236. Said differently, a connector housing 230 can be provided by joining two symmetrical stamped housing sections 200 about an interface 236 to form the housing groove 240, which forms an external groove for mounting a spring 148 that faces a bore of an external housing 85, such as a sleeve. The length of the bottom wall 210 can be adjusted to determine the width of the housing groove 260 or be dependent on the type and/or size of the spring 148 to be accommodated. Similarly, the length of the sidewall 214 of the housing section 200 can be selected to control a groove depth and the angle between the sidewall 214 and the bottom wall 210 can be adjusted to determine the depth of the housing groove 240 or to form a bottom groove without a flat bottom. As previously alluded to, the term stamped housing section 200 does not preclude some machining, such as to fine tune certain geometries of the housing sections 200 to fine tune the completed connector housing 230. The connector housing 230 can also be machined to certain modified dimensions.

With reference to FIGS. 12, 13, and 16-18, a single housing section 200 can be coupled to, mate, or abut against a surface 60 of a housing body 65 to form a connector housing 230. Thus, the embodiments described have at least one housing section having a stamped or coined surface. The surface 60 for joining can be flat or curved or irregular and can be part of a flange, a plate, a frame, etc. In the illustrated embodiment, the surface 60 of the housing body 65 is flat. The outer perimeter 204 of the housing section 200 can be situated close to, such as aligned with, the outer perimeter 64 of the body 65. The inner perimeter 66 of the body 65 can be substantially similar to the size of the bore 206. The housing groove 240 is cooperatively defined by the sidewall 214 of the housing section 200, the bottom wall 210, and the surface 60 of the body 65. The length of the bottom wall 210 can be adjusted to determine the width of the housing groove 240 or be dependent on the type and/or size of the spring 148 to be accommodated. Similarly, the length of the sidewall 214 of the housing section 200 can be adjusted to determine the depth of the housing groove 240. The bottom wall 210 of the housing section 200 can be perpendicular or form an angle with the surface 60 of the body 65. The sidewall 214 of the housing section 200 can be parallel or form an angle with the surface 60 of the body 65.

With reference to FIGS. 13 and 18, the body 65 can have an opening, channel, or path, or bore 55 through the surface 60 to allow a conductive lead 70 to pass through the body 65 and electrically connect to the housing section 200. The conductive lead can be welded to the housing section 200. The conductive lead 70 can alternatively be pressed fit to the opening or bore 55 of the housing body 65.

The canted coil spring 148 can be similar to one of the springs discussed elsewhere herein.

With reference to FIGS. 10-18, the housing section 200 is substantially similar to the housing section 100 of FIGS. 1-4 except that the sidewall 214 is extending outwardly away from the central axis of the housing and therefore is configured to be used differently and for forming an external groove 240. When one housing section 200 is connected to another housing section 200, an external housing groove 240 is formed. Similarly, the spring 148 can be placed in the recessed space 220 of one of the housing sections prior to joining the two housing sections 200 together. The housing section 200 can be used in a bore 80 of an external housing 85. The bore 80 of the external housing 85 can have an internal groove 84. The internal groove 84 can have a bottom wall 82 and two sidewalls 88a, 88b which can be substantially parallel to each other. In other examples, the wall surfaces 88a, 88b can be tapered and converge to the bottom wall 82 or to a point (i.e., no bottom wall). In still other examples, the bottom wall 82 can have a single taper relative to the other sidewall 88a, 88b. In yet other examples, one sidewall 88a, can be vertical while the other sidewall 88b is slanted or tapered or vice versa. The external housing 85 can be connectable to other components. For example, the outer housing 85 can be connected to a first object and the connector housing 230 to a second object for securing the first object to the second object via the connector assembly or for electrically connecting the first object to the object via the connector assembly 20. The outer diameter 155 of the spring 148 is greater than the bore 80 of the housing. The outer perimeter of the housing section 200 and the connector housing 230 is less than the diameter of the bore 80 of the external housing 85.

During assembly, the spring 148 can be placed in the recessed space 220 of a first of two housing sections 200 and then a second housing section 200 is attached to the first housing section 200. Alternatively, the spring 148 can be placed in the recessed space 220 of the first housing section 200 and then together mounted to the surface 60 of a housing body 65. This allows the spring 148 to be installed within the connector housing 230 with minimal deflection and stress to the spring 148, which in turn reduces the possibility of mis-orientation of the spring contact within the housing groove 240. The installation of the spring 148 into the spring groove when the housing section 200 is already joined to the other housing section 200 would require deflecting the spring 148 a significant amount to fit the spring 148 through the housing bore diameter and then once through the bore diameter, the spring 148 can expand into the housing groove 240. However, this process can lead to the spring 148 being tilted or mis-oriented within the groove upon expanding, thus possibly resulting in a high force insertion or removal of the pin 40 in through the bore 206 of the one-piece connector housing 230 such as by having the pin 40 contacting the spring 148 closer to the major axis of the spring coils. The groove is sized and shaped to accommodate a canted coil spring 148, which is shown as an axial canted coil spring with a radial canted coil spring contemplated. While only two coils are shown, the canted coil spring 148 is understood to include a plurality of coils all canted in the same direction. Furthermore, it is understood that the spring will only deflect along one of two coil axes. However, it is contemplated that the presently disclosed connector housing can be used with a canted coil spring after two housing sections are joined.

The connector assembly (10, 20) of the present disclosure can be used in or as a component of devices in which a connector is removably or permanently coupled to another connector or housing. As such, the connector assembly (10, 20) can be used in a wide variety of applications in which a spring groove is used to retain a spring and wherein a connection is to be made between a pin and a connector housing with a spring, such as an implantable medical device (IMD).

In one such example, the connector assembly (10, 20) can substitute the conductive contact element in the implantable medical device disclosed in U.S. patent application Ser. No. 14/025,682, published as US Publication No. 2014/0079476, the relevant portion of which is herein incorporated by reference. For example, the implantable medical device can comprise a can housing, a header, and an in-line connector stack comprising a plurality of connector components having a common bore for receiving a lead cable. Exemplary IMDs, such as implantable cardio defibrillators, pacemakers, and programmable neuro-stimulator pulse generators are herein referred to as "implantable medical devices" or IMDs. IMDs and in-line connectors are disclosed in U.S. Pat. No. 8,437,855, the contents of which are expressly incorporated herein by reference. The can housing is a hermetically sealed device enclosing a power source and electronic circuitry for passing signals to the lead cable via the in-line connector.

The header has a bore for receiving the in-line connector stack, which comprises a plurality of seal elements, connector assemblies (10, 20), and springs. The seal elements are each configured to seal against the bore of the header and against the exterior surface of the lead cable. The spring contacts are configured to bias against the electrical terminals of the lead cable to pass signals or current from inside the can housing, through the connector assemblies (10, 20), through the springs, to the electrical terminals, and to the electrode leads located inside the lead cable and extending to the various parts of the human body to provide electrical stimulation to the body tissues.

An in-line connector stack can comprise a plurality of connector components located inside an encapsulation layer, which is configured to retain or hold the in-line connector stack away or outside of the header. The encapsulated stack which comprises the encapsulation layer surrounding and retaining the in-line connector stack outside of a header, can also have a mounting pin which resembles a lead cable except it is solid and does not carry electrode leads. The mounting pin facilitates stacking of the various components for assembling purposes. The encapsulated stack can be assembled with a plurality of alternating seal elements and connector assemblies (10, 20), each comprising a spring contact element to form the in-line connector stack.

The encapsulated stack would allow the integrity of the in-line stack to be tested outside of a header and before it is installed in an IMD. For example, conductive leads may be attached to corresponding connector assemblies (10, 20) through windows provided through the encapsulation layer, such as by welding or soldering the leads to the interface of the connector assemblies (10, 20). Thus, the windows on the encapsulation layer as well as the conductor leads are aligned with corresponding interfaces of two adjacent connector assemblies (10, 20). Test current or signals may be applied through the conductor leads to test the operability of the in-line connector, such as to test current sent to the connector assemblies (10, 20) via the conductor leads. The stack can also be tested by holding the components that form the connector assemblies (10, 20) together with the spring contacts installed in the connector assemblies (10, 20) and inserting a lead to find insertion, removal, and frictional forces, and electrical performance. Exemplary encapsulated stacks and encapsulation layers but without the unique stamped features of the present device, system, and method are disclosed in U.S. Pat. No. 8,215,013, the contents of which are expressly incorporated herein by reference.

With reference now to FIGS. 19A and 19B, cross-sectional views of two similar canted coil springs 148 with a plurality of coils 36 (only one shown) all canted generally along a same canting direction, such as cant in the same direction of a coil centerline, and wherein at least one of the coils has a coil shape defined by two generally parallel straight segments 270 with an elliptical segment 272 at each end that joins the two generally parallel straight segments 270 together installed in a rectangular groove 274 of a housing 276. Each coil 36, for a typical radial canted coil spring, has a coil height CH or shorter of two axes, which is generally orthogonal to the connector centerline, $\mathcal{C}_L$, and a coil width CW or longer of two axes, which is generally parallel to the connector centerline, $\mathcal{C}_L$. However, as the canted coil springs of the present disclosure are modified, the axes of the coils that deflect radially of the coil centerline can be the longer or the shorter of two axes. Thus, a coil height CH can be longer than a coil width CW and the coils can still deflect along the coil height, as further discussed below. Accordingly, in some instances, when called out, the coil height CH can be designated as the shorter of two axes of the coil 36 or the longer of two axes of the coil 36 due to the present disclosure's modification of the coils and therefore how they can deflect or cant, as further discussed below.

The dimensions of the canted coil spring 148, such as coil height CH and coil width CW, the coil shape, and which of the two axes will cant, can be altered to the dimensions of the specific application, such as to the specific shape or dimension of a groove or for a specific spring force characteristics. Due to the generally parallel straight segments 270 joined by two elliptical segments 272, the canted coil spring 148 may produce a lower CH/CW ratio, as depicted in FIG. 19A, or a relatively higher CH/CW ratio, as depicted in FIG. 19B, while leaving the deflected coil height (DCH), groove depth (GD), and groove width (GW) unaltered. In other words, in both the FIG. 19A embodiment and the FIG. 19B embodiment, the coils 148 deflect in a radial direction relative to the lengthwise axis of the connector assembly 280, which is radial of the respective connector centerline, $\mathcal{C}_L$, even though in the two figures, the orientation of the longer axis differ. Thus, although the longer axis of the coils 36 spring of FIG. 19B is orthogonal to the centerline of the assembly and appears to be an axial spring, the spring is a radial canted coil spring and is coiled to cant along the longer of two axes of the coils, such as cant in the radial direction to the centerline. In contrast, existing prior art canted coil springs with elliptical coils deflect or cant along the shorter of the two axes only. In the present embodiment, canting only along the shorter of the two axes may or may not apply, which is a unique feature not present in prior art canted coil springs. Thus, the canting can take place along the longer of two axes or the shorter of two axes. The direction of canting can be formed by turning the coils so that they all cant in the same direction while also controlling the coil height CH and coil width CW during coiling. The process of coiling the various canted coil springs described herein can be accomplished using a programmable machine having multi-axes capabilities for bending or coiling a wire to form the desired shape.

Thus, an aspect of the present disclosure is understood to include a canted coil spring having a coil height CH and a coil width CW and wherein the coil deflect along the coil height CH, which can be longer than the coil width CW, the same as the coil width CW, or shorter than the coil width CW. As shown in FIG. 19B, the canted coil spring 148 comprises a plurality of coils 36 and wherein each coil has a first coil axis and a second coil axis, which is longer than the first coil axis, and wherein the second coil axis defects or cants in a radial direction, orthogonal to the centerline $\mathcal{C}_L$ of the connector assembly 280.

The canted coil spring's generally parallel straight segments 270 form line contacts with adjacent contacting surfaces of the housing 276 and the pin 282, which prevent the spring 148 from rolling or rotating while in the groove 274. Additionally, the present connector embodiments provide increased contact surface areas compared to prior art contacts between a pin and/or a housing and a typical curvature of an elliptical coil. For example, with prior art curved coil shapes, contact areas between the coils and the adjacent contact surfaces, such as the housing and/or pin, are generally contact points rather than line contacts. In the present embodiments utilizing parallel straight segments 270, the coils 36 contact with the straight edge of the piston and the straight edge of the housing groove bottom (FIG. 19A), which contact across larger surface areas compared to point contacts, such as a curved surface contacting a flat surface. Looking at FIG. 19B, the parallel straight segments 270 contact the straight housing groove sides or sidewalls (FIG. 19B), which is especially advantageous in electrical applications, where increased in contact areas is generally more desirable for better electrical conductivity.

The groove 274 may be part of a housing 276, which has a bore 106 for receiving a pin, piston or shaft 282. The pin 282 is shown without a pin groove, which in other embodiments can be incorporated, such as shown in FIGS. 2, 6, and 8. The pin groove can have different groove geometries to function as a latching connector and permit the pin to separate from the housing or a locking connector that does not allow the pin to separate from the housing. Further, the housing 276 can be machined or can be the same as one of the multi-part housings of FIGS. 1-18, which has at least one housing section having a stamped section cold worked and shaped with a die. In other words, the canted coil spring 148 of FIGS. 19A and 19B may be used with any of the connectors 10, 20 of FIGS. 1-18.

FIGS. 20A, 20B, and 20C show three different canted coil springs 148 each comprising a plurality of coils 36 all with polygonal geometries located in a groove 274 of a housing 276, which may be any of the connector housings shown and described with reference to FIGS. 1-18 or with a machined housing with a machined housing groove. The specific polygonal geometry of the coils 36 may be adapted to the particular groove geometry that each spring 148 is positioned in or installed into. Coils 36 with such polygonal geometries can be, for example, a pentagonal shaped coil 290 with two right angles 292 for use in a groove 274 having two generally parallel sidewalls 294 and a flat bottom wall 298 located therebetween (FIG. 20A), an equilateral pentagonal shaped coil 290 for use in a groove 274 with chamfered surfaces 296, which has a flat bottom wall 298 located between two tapered sidewalls 296 (FIG. 20B), or a rhombus-shaped coil 290 for use in a groove 274 with a V-bottom (FIG. 20C). The V-bottom of FIG. 20C can also include a lip to accommodate part of the two side apexes of each coil. In other examples, the canted coil springs 148 of FIGS. 20A-20C are usable with the multi-part housings of FIGS. 1-18, each of which having at least one housing section having a stamped section shaped with a die and wherein the housing sections of a connector housing are shaped to have corresponding surfaces to accommodate polygonal shaped springs, or vice-versa—the springs coiled with a certain shape to fit the housing groove geometry.

Due to adaptation of the polygonal geometries of the coils 290 of the canted coil spring 148 of the present disclosure to the particular groove geometries they are installed into, the canted coil springs are able to maintain their position with little to no spring rolling. This allows for better control of insertion and removal forces as well as slip prevention in rotary applications. Additionally, increased contact areas are provided by the straight coil segments 270 of the springs 148 abutting against the straight edges of the housing groove sides. This increased in contact areas is especially advantageous in electrical applications where greater contact areas are desired for better electrical conductivity. Other coil geometries may also be implemented, such as isosceles triangle, right triangle, rectangle, parallelogram, pentagon, five-sided, six-sided or higher.

Thus, an aspect of the present disclosure is understood to include a canted coil spring 148 comprising a plurality of interconnected canted coils 36 each with a complex coil shape. In an example, the coil has a polygonal shape. In some examples, the polygonal shape structure is a pentagonal shaped coil. In other examples, the polygonal shape structure is an equilateral pentagonal shaped coil. In still other examples, the polygonal shape structure is a rhombus-shaped coil. The polygonal shape structure can also be rectangular. The polygonal shaped coils are configured to be positioned into grooves having partially matching contours. For example, in the embodiment of FIG. 20A, the two generally parallel and straight sides with a flat bottom side of the pentagonal shaped coil is configured to fit into a matching square shaped groove, which has two generally parallel sidewalls and a flat bottom wall. The housings with grooves that the springs of FIGS. 20A-20C can be used with can be machined or can be one of the connector housings disclosed elsewhere herein made from multi-pieces in which at least one of the housing sections of the connector housing has a stamped section and a contour formed by cold working a blank with a die.

FIGS. 21A and 21B show cross-sectional views of two types of canted coil springs 148 each with a plurality of coils 36 and wherein each coil has a geometry where angle α can determine insertion force and angle β can determine removal force when used in a mechanical connector. Each coil 36 has a coil height CH and a coil width orthogonal to the coil height. The coils deflect along the direction of the coil height CH. Due to the canted coil springs' geometries with controllable angles α and β, piston insertion and removal forces, such as when used with the assembly of FIG. 2 and the pin 40 is inserted into the housing 130 to generate an insertion force and subsequently removed to generate a removal force, can be controlled by configuring the angles α and β of the coils 36 of the canted coil spring 148 without the need to modify the angles of the pin groove, the housing groove, or both grooves, to control the insertion and removal forces. Said differently, for the same combination of pin and housing and certain groove geometries, different insertion and disconnect forces can be obtained by taking the same canted coil spring but varying angles α and β. Different combinations of sliding, insertion and removal forces can be obtained given the same pin and housing but changing the shape of the coils 36 of the canted coil springs 148 usable with the same pin and housing, such as changing different coil springs with coils having different angles α and β, as depicted in FIGS. 21A and 21B. This design is especially advantageous in easy disconnect applications when low insertion force to insert a pin and high removal force to remove the pin are desired. In both examples, angle α is less than angle β.

Assume that the canted coil springs of FIGS. 21A and 21B are both located in a housing groove and a pin is inserted into the spring and the housing bore from left to right relative to the viewing perspective of FIGS. 21A and 21B, insertion forces will be lower, when moving the pin left to right, than removal forces, when removing the pin by moving from right to left. The smaller angle, such as angle α in the two springs shown in FIGS. 21A and 21B, is formed by providing a long coil segment 300 connected to a relatively shorter coil segment 302, which creates a larger angle β so that the segments of the coil connect. When engaged by a pin, such as during insertion by moving from left to right and removal by moving from right to left, the segment of the coil with the smaller angle more readily defect than the segment with the larger angle, which produces lower insertion forces than removal forces.

Conversely, for the same springs of FIGS. 21A and 21B, same housing groove, and same pin groove, but insertion of the pin is from right to left and removal is from left to right, the insertion forces will be higher than the removal forces due to the relative positions of angle α and angle β and the direction of movement of the pin. In other words, the pin will contact the coil segment with the larger angle β first during insertion and will interact with the coil segment with the smaller angle α second during removal or retraction thereby producing removal forces that are less than insertion forces.

Figure 22:
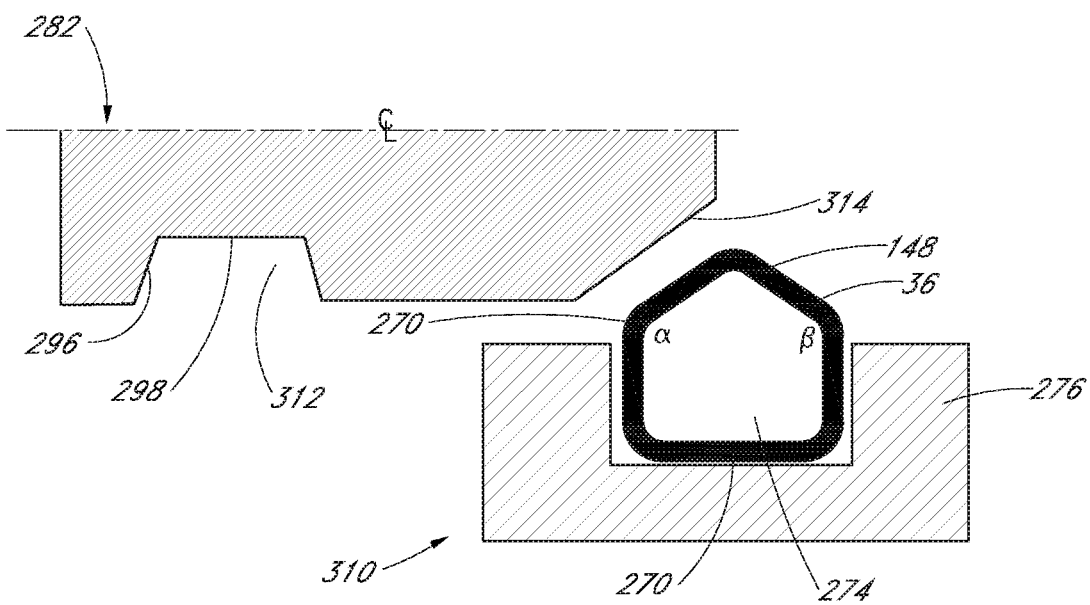
FIG. 22 shows a cross-sectional view of a canted coil spring in a connector assembly with pentagonal geometry where angle α is about the same as angle β, said spring installed in a correspondingly sized rectangular housing and approached by a pin with latching groove.

FIG. 22 shows a cross-sectional view of a connector assembly 310 comprising a housing 276 having a housing groove 274, a pin 282, which can also be called a piston or a rod, with a pin groove 312, a tapered insertion end 312, and a canted coil spring 148 located in the housing groove 274, or is housing mounted. The spring 148 has a plurality of canted coils 36 (only one shown) and wherein the shaped of each coil is a pentagonal shaped geometry where angle α is equal to angle β. Reference to angles α and β are taken from the same locations or positions as that of FIG. 21B. The canted coil spring 148 is installed in a correspondingly sized rectangular housing groove 274 and approached by a pin 282 with a latching groove 312. The pin groove 312 has a bottom surface 298 and two chamfered sidewalls 296 for accepting the two straight coil segments 270 that are angled relative to one another. The geometry of the coil 36 shown may be pentagonal with two right angles for use in a flat housing groove 274 or an equilateral pentagonal shaped coil for use in a chamfered groove, similar to the groove of FIG. 20B. The insertion and removal forces will be approximately the same given a pin with a symmetrical groove and angles α and β on the coils being generally the same. However, as discussed above, the angles on the coils can be modified so that angles α and β have different angle values. Due to the pentagonal shaped geometry of the coils of the canted coil spring with controllable angles α and β, piston insertion and removal forces to latch and unlatch from the housing 276 can be controlled by modifying the angles of the coils 36 of the canted coil spring 148 without the need to also modify the angles of the pin groove 312, the housing groove 274, or both grooves. Different combinations of sliding, insertion and removal forces can be obtained given the same pin and housing grooves but with canted coil springs having different angles α and β, such as discussed above with reference to the springs 148 of FIGS. 21A and 21B. The connector assembly 310 of FIG. 22 is especially advantageous in certain applications where insertion and removal forces are desired to be equal, by adopting approximately the same angles α and β for the coils 36 of the canted coil spring 148. In other examples, the angles α and β of the coils 36 of FIG. 22 can be altered to have different values.

The springs in the following embodiments may be assumed to be usable with a machined housing having a groove or with one of the multi-part housings of FIGS. 1-18, discussed above, wherein each multi-piece housing has at least one housing section having a stamped section shaped by cold working with a die and wherein the housing sections of the multi-piece housing, and particularly the housing groove formed thereby, are shaped to accommodate the unique spring coil shapes discussed herein.

FIGS. 23A and 23B show cross-sectional views of canted coil springs 148 with coils (only one shown) 36 having pentagonal geometries where angle α is not equal to angle β. The coils 36 also have a straight segment 270 connected to two additional segments 270 at defined angles 320, which can be right angles. However, these defined angles 320 can be acute or obtuse angles. Reference to angles α and β are taken from the same locations or positions as that of FIG. 21A or FIG. 21B.

The geometry of the coil 36 may be pentagonal shaped with two right angles 320 for use in a flat housing groove 274 (FIG. 22), or with equally slanted sides for use in a chamfered housing groove, similar to FIG. 20B. If insertion forces are desired to be less than removal forces, assuming insertion direction of a pin is left to right and removal is right to left, the spring 148 of FIG. 23A may be used, where angle α is less than angle β. Alternatively, if insertion forces are desired to be greater than removal forces, the spring 148 of FIG. 23B may be used, where angle α on the coil 36 is greater than angle β. Due to the canted coil spring's pentagonal shaped geometry with controllable angles α and β for the coils 36, piston insertion and removal forces can be controlled by alternating the angles on the coils 36 of the spring 148 without the need to modify the angles or shapes of the pin groove 312, the housing groove 274, or both. Different combinations of sliding, insertion and removal forces can be obtained given the same pin and housing groove geometries but whereby the coils with angles α and β are altered, as discussed elsewhere herein. The spring 148 of FIG. 23A is especially advantageous, with coils in which angle α is smaller than angle β, when using in a latching connector application where low insertion and high removal forces are desired, again assuming the same mounting orientation for angles α and β and insertion and removal directions for the pin. For the same connector assembly but using the spring 148 of FIG. 23B, the insertion forces will be higher than the removal forces due to the changed angles α and β.

FIGS. 23C and 23D show cross-sectional views of canted coil springs 148 having a plurality of coils 36 (only one shown) each with right trapezoidal geometries where angle α is not equal to angle β. Reference to angles α and β are taken from the same locations or positions as that of FIG. 21A or FIG. 21B. The same insertion and removal directions are also assumed when the springs 148 shown are used with a connector assembly comprising a housing with a groove and a pin with a groove. However, the pin can also not include a groove in a holding application. If insertion forces are desired to be less than removal forces, the spring 148 of FIG. 23C may be used, where angle α is less than angle β. If insertion forces are desired to be greater than removal forces, the spring 148 of FIG. 4D may be used, where angle α is greater than angle β. Due to the canted coil spring's trapezoidal geometry with controllable angles α and β for the coils 36, piston insertion and removal forces can be controlled by altering the angles α and β on the coils of the canted coil spring 148 without the need to modify the angles of the pin groove, the housing groove, or both. Different combinations of sliding, insertion and removal forces can be obtained given the same pin and housing groove geometries but whereby the coils with angles α and β are altered, as discussed elsewhere herein. The spring 148 of FIG. 23C is especially advantageous in applications when low insertion and high removal forces are desired as angle α is smaller than angle β. For the same connector assembly but using the spring 148 of FIG. 23D, the insertion forces will be higher than the removal forces due to the changed angles α and β.

FIGS. 23E and 23F show cross-sectional views of canted coil springs 148 comprising a plurality of coils 36 (only one shown) with pentagonal shaped geometries where the coil height and wire thickness are increased, respectively, as compared to the springs 148 of FIGS. 23A-23D. By increasing the coil height (FIG. 23E), both insertion and removal forces may be increased due to the larger angles α and β (in comparison to angles α and β incorporated with the coils 36 of FIG. 4).

The canted coil spring 148 of FIG. 23F has coils 36 with pentagonal shaped geometries. However, the spring 148 is formed using a heavier wire to form the coils of the spring, which has the same shape as the coils of FIG. 22. By using the heavier wire, sliding, insertion, and removal forces when the canted coil spring 148 is used with a housing and a pin may increase due to increased strength of the canted coil spring material, as compared to the same shaped coils and same angles α and β. When combined with the previous embodiments (increasing angle α/angle β, decreasing angle α/angle β) and available angle variations of the various coils, these modifications to the canted coil springs 148 themselves can achieve the desired insertion and removal forces. Thus, due to canted coil spring geometries where coil height and wire thickness are varied, piston insertion and removal forces can be controlled by controlling aspects of the spring itself, such as angles, wire diameters, and coil height, without the need to modify the angles of the pin groove, the housing groove, or both grooves. Different combinations of sliding, insertion and removal forces can be obtained by varying aspects of the spring only for the same pin and housing.

FIG. 24 shows a connector assembly 330 comprising a housing 332 and a pin 334, which has a centerline ℄ and a pin insertion end with a chamfered surface (not shown). Unless indicated otherwise, the pins or pistons disclosed herein are solid or have solid cores and have an end surface or end wall adjacent the insertion end. FIG. 24 shows a cross-sectional view of three canted coil springs 148, each with a plurality of coils 36 (only one shown). Each coil 36 has a non-elliptical and non-rectangular shape and comprises an interior loop 336 that is located entirely within the outer contour of the coil 36. The loop 336 forms a dimple 338 on one of the sides of the coil 36. As shown, the dimple is a concave segment on a side of the coil, which produces two lips or two contact points on either side of the concave segment for producing two contact points when contacting a surface. Thus, compared to a straight edge, the dimple 338 side of the coil forms two contact points 340 for contacting the pin surface, which can be flat or includes a convex protrusion, as discussed below.

The three canted coil springs 148 are inserted into three correspondingly sized rectangular grooves 274 of the housing 332 and a piston or pin 334 with three corresponding convex protrusions 342 contact the coils. Due to the unique cross-sectional shape of the canted coil spring 148 of FIG. 24 as well as the corresponding convex protrusions 342 of the piston 334, a latch connection can be accomplished when the protrusions 342 rest in the dimples 338 of the coils 36. In other words, a latch connection can be accomplished with the present connector assembly 330 without incorporating a pin groove, as is typically required in prior art latching connectors that utilize a housing with a housing groove and a pin with a pin groove and wherein a canted coil spring is captured between the two grooves in a latching application. The same latching concept can be practiced in a connector assembly of the present disclosure using only a single canted coil spring 148 instead of three, as shown with reference to FIG. 25. The latching connector can also be practiced with more than three canted coil springs 148 and more than three housing grooves. Latching, as used herein, is understood to mean securing a pin to a housing using more than just friction forces and biasing forces of the spring, which is understood to be a holding application. As disclosed, the connector assembly 330 is a latching connector in that the latching requires a certain force, i.e., removal force, to deflect the springs in order for the pin to separate from the housing. For a holding application, removal of the pin simply requires overcoming the friction force between the coils and the surface of the pin during retraction of the pin without further canting or further deflecting the coils of the canted coil spring during the retraction. As shown, to separate the pin 334 from the housing 332, the coils must be deflected, such as by pulling the pin so that the protrusions ride against the dimples 338, so that the low point of the protrusions 342 can cant the coils 36 to then slide past the dimples 338 and the pin to separate from the housing 332.

Thus, an aspect of the present disclosure is understood to include a latching connector wherein a groove in the pin or a groove in the housing is incorporated but not both. In a particular example, the groove is in the housing and the pin comprises a convex protrusion for engaging a dimple on each of a plurality of coils of a caned coil spring.

Additionally, the multiple contact points between the canted coil spring coils 148 and the piston 334, as provided by the dimples 338, and the increased contact areas provided by the straight coil segments along other segments of the coils against the straight housing groove bottoms of the three housing grooves is especially advantageous in electrical applications, where more contact points or increased contact areas is desired for better electrical conductivity. The coils are also more stable within the housing groove and less prone to rolling due to the larger surface contacts between the straight segments of the coils and the surfaces of the housing grooves.

The use of multiple springs 148 in a connector assembly allows for multiple contacts in parallel, whether it is for higher current capabilities or for a higher number of electrical channels. Due to the canted coil springs' rectangular shape lower sections abutting against the bottom surfaces of the housing grooves, wherein the straight coil segments contact the groove bottoms, the canted coil springs are able to maintain their positions with little to no spring rolling. This allows for better control of insertion/removal forces as well as slip prevention in rotary applications.

Figure 25:
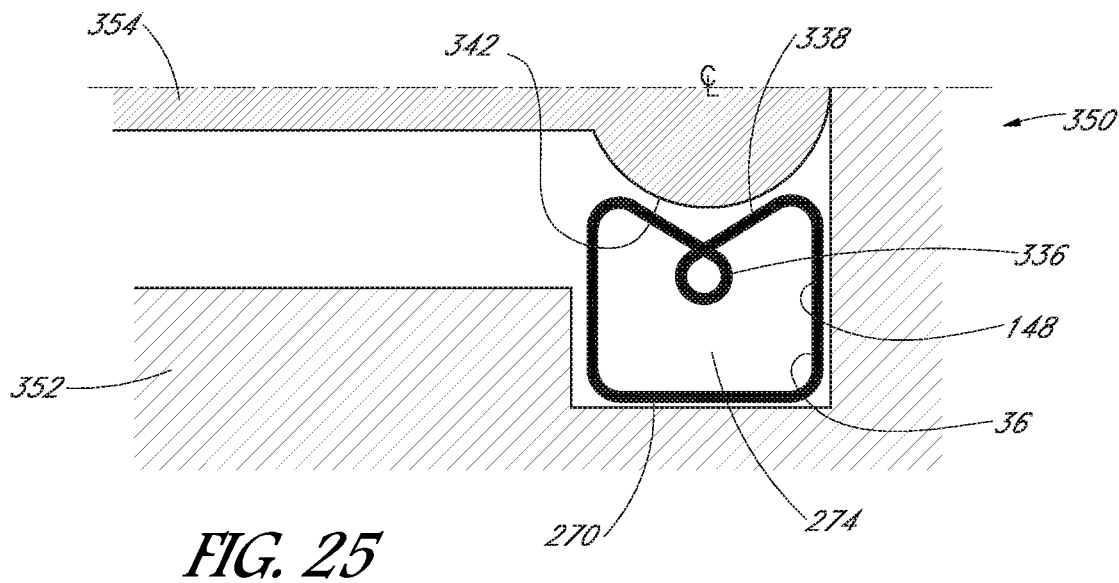
FIG. 25 shows a cross-sectional view of a canted coil spring, said cross-sectional view showing a coil being a non-elliptical and non-rectangular shape and comprising at least an interior loop that is entirely within said coil contour and positioned in a housing with a correspondingly sized rectangular groove and a piston with a corresponding convex protrusion contacting the dimple formed by the interior loop.

FIG. 25 shows a connector assembly 350 having a housing 352, a pin 354, and a canted coil spring 148 comprising a plurality of coils 36 (only one shown). FIG. 25 shows the canted coil spring 148 having a non-elliptical and non-rectangular shape and comprising at least an interior loop 336 that is entirely within the outer contour of the coil's complex shape. The interior loop 336 creates a dimple 338 along one of the sides of the coil 36. The canted coil spring 148 is inserted or positioned into a housing groove 274 of the housing 352 with a correspondingly sized rectangular groove 274 so that at least the bottom straight segment of the coil 36 contacts the groove bottom of the housing groove 274. The piston or pin 354 has a convex protrusion 342. This geometry ensures contact between the canted coil spring 148 and the pin 354, latching the pin, and more particularly the convex protrusion 342, in the dimple 338 of the spring 148 while also allowing for pin rotation relative to the housing 352. Due to the unique cross-sectional shape of the canted coil spring 148 with the dimple 338 as well as the corresponding convex protrusion 342 of the piston 354, a latch connection can be accomplished without incorporating a groove in both the pin and the housing. Instead, a single groove in the housing 352 is incorporated to form the latching connector of the present disclosure. In an example, a convex protrusion 342 formed on the exterior of the pin 354 is sized and shaped to engage a dimple 338 formed on one of the sides of coils 36 of the canted coil spring 148.

Additionally, multiple contact points are formed by incorporating the dimple 338. For example, at least two contact points are present between the coils 36 of the canted coil spring 148 on the side of the coil with the dimple 338 contacting the piston 354. The convex surface on the pin produces two contact points with the coil at the dimple. However, pin can have a flat surface and still produce two contact points with the coil at the dimple. This increases the number of contact points compared to a normal convex arc typically found with prior art coils. The contact areas are also increased by other parts of the coils, such as where the straight coil segments 270 of the plurality of coils 36 abutting against the straight housing groove bottom. This is especially advantageous in electrical applications where more contact points are contact areas are desired for better electrical conductivity. Due to the canted coil spring's rectangular shape along a lower end, such as the straight segments 270, abutting against the housing groove bottom, the canted coil spring is able to maintain its position with little to no spring rolling during installation and during pin insertion and removal. This allows for better control of insertion/removal forces as well as slip prevention in rotary applications.

Figure 26A:
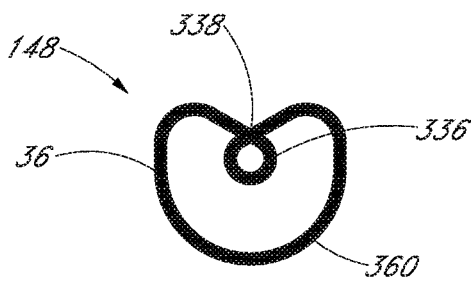
FIG. 26A shows a variation of the canted coil spring shown in FIG. 25 in a cross-sectional view showing a coil of the canted coil spring being a non-elliptical and nonrectangular shape and comprising at least an interior loop that is entirely within said coil contour.

FIG. 26A shows a variation of the canted coil spring 148 shown in FIG. 25. FIG. 26A shows a cross-sectional view of a canted coil spring 148 having a plurality of non-elliptical and nonrectangular shape coils 36 (only one shown) each comprising at least one interior loop 336 that is located or arranged entirely within an outer contour of said cross-sectional profile. The loop 336 forms a dimple 338 on one of the sides of the coil 36. Whereas the base of the coil in the cross-sectional view of FIG. 25 is flat and rectangular, the base 360 of the coil in the cross-sectional view in FIG. 26A is curved. Due to the unique cross-sectional shape of the canted coil spring 148 of the present embodiment as well as the corresponding convex protrusion 342 of a piston 354 usable with the spring 148, such as the piston 354 of FIG. 25, a latch connection can be accomplished without incorporating a pin groove, although it is possible to use the present spring with a convention pin groove in a latching connector application. Additionally, multiple contact points between the coil 36 of canted coil spring and the piston 354 is especially advantageous in electrical applications, where more contact points are desired for better electrical conductivity. Due to the canted coil spring's multi-contact design, the canted coil spring 148 of the present embodiment is able to maintain its position with little to no spring rolling. For example, a housing groove with straight sidewalls and a curved bottom to match the base 360 of the spring 148 will allow the spring to seat within the housing groove in a very stable condition with little to no spring rolling. This allows for better control of insertion/removal forces as well as slip prevention in rotary applications.

Figure 26B:
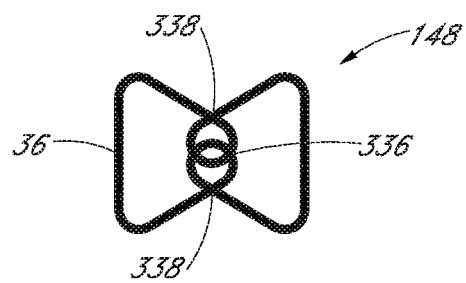
FIGS. 26B, 26C, and 26D show cross-sectional views of three canted coil springs each having a coil being non-elliptical and non-rectangular shape and comprising at least an interior loop that is entirely within said coil contour.
Figure 26C:
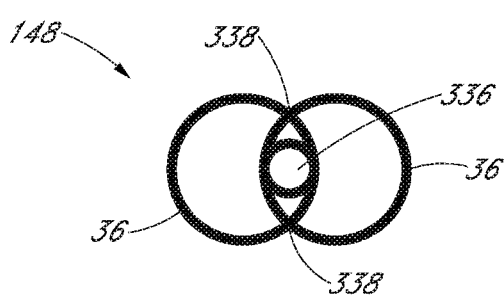
Figure 26D:
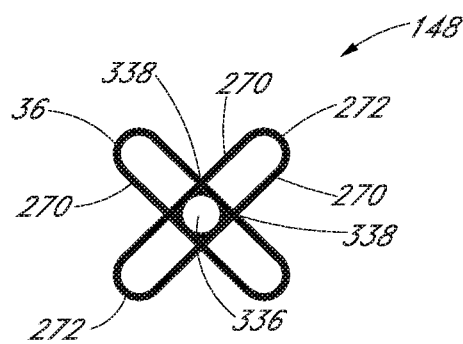

FIGS. 26B, 26C, and 26D show cross-sectional views of three canted coil springs 148 each spring with a plurality of coils 36 (only one shown). The cross-sectional views of each of said canted coil springs showing a coil with a non-elliptical and non-rectangular shape and comprising at least an interior loop 336 arranged entirely within an outer contour of said coil. Said cross-sectional views showing a coil 36 with a bow tie shape (FIG. 26B) in which two dimples 338 are formed on an exterior of two of the sides of the coil, an infinity or number "8" shape with two circular coils having an interior loop 336 (FIG. 26C) and two dimples 338, or sets of generally parallel straight segments 270 each joined by elliptical segments 272 (FIG. 26D) to form an "X" shape having an interior loop 336. The canted coil spring 148 of FIG. 26D has four external dimples 338. Due to the unique cross-sectional shapes of the canted coil springs 148, the number of contact points between the piston or pin and the canted coil spring 146 of FIGS. 26A-26D and between the housing and the canted coil spring 148 of FIGS. 26A-26D, when said springs are used in a connector assembly having a housing and a piston, can increase due to the dimple or dimples, straight, and curved segments incorporated in those springs. This multi-contact design is especially advantageous in electrical applications, where more contact points are desired for better electrical conductivity. Due to the adaptation of the canted coil springs' multi-contact design, the canted coil springs are able to maintain their position with little to no spring rolling. This allows for better control of insertion/removal forces as well as slip prevention in rotary applications.

Figure 27:
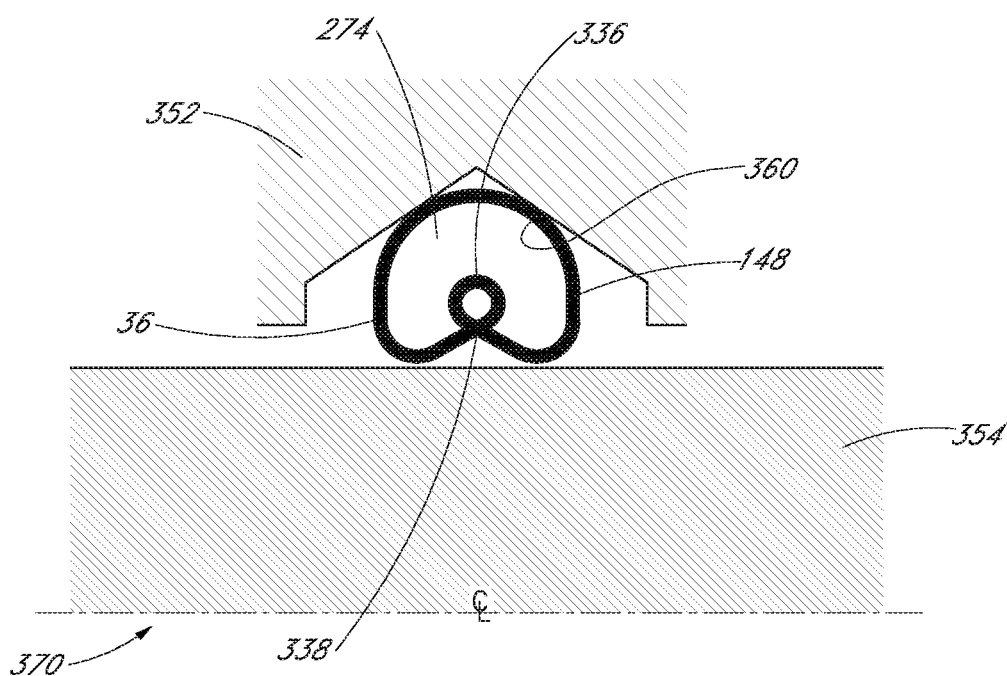
FIG. 27 shows the spring of FIG. 26A positioned in a housing groove in contact with a shaft or pin.

FIG. 27 shows a connector assembly 370 with a canted coil spring 148 comprising a plurality of coils 36 (only one shown) located in a housing groove 274 of a housing 352 and contacting a shaft or pin 354. The pin 354 does not incorporate a pin groove, or a convex projection, and the connector application is readily recognized as a holding application. The spring 148 with the coil shape shown is similar to the spring of FIG. 26A. Due to the shape of the cross-sectional profile of the coils 36, each coil is able to achieve two contact points with the straight shaft or pin 354. As discussed above, each coil 36 has an interior loop 336 to form a dimple 338 on one of the sides of the spring coil. The dimple forms a concave or recess section or segment on one of the sides of the coil to define two contact points. Additionally, two points of contact are provided between the housing 352 and the curved base 360 of the canted coil spring 148, accomplished with the use of a V-bottom groove 274, which has two slanted surfaces converging at a point. These features may improve performance of electrical connectors.

Figure 28:
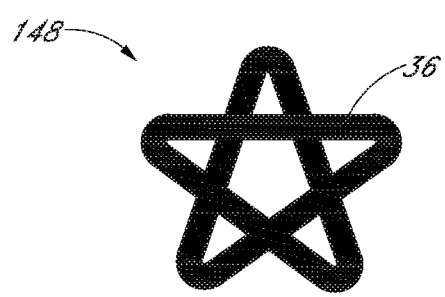
FIG. 28 shows a cross-sectional view of canted coil spring having coils with a star-shaped geometry with wire of the canted coil spring following a pentagram pattern.

FIG. 28 shows a cross-sectional view of canted coil spring 148 comprising a plurality of coils 36 (only one shown) each with a non-elliptical and non-rectangular shape. As shown, the coil has a star-shaped geometry with the wire of the canted coil spring following a pentagram pattern. Due to the unique cross-sectional shape of the canted coil spring 148, the number of contact points between the piston or pin and the canted coil spring 148 and between the housing and canted coil spring 148, when the spring 148 of FIG. 28 is used in a connector assembly with a housing and a pin, can increase, assuming the groove is chamfered and fitted. This multi-contact design is especially advantageous in electrical applications, where more contact points are desired for better electrical conductivity. Due to the canted coil spring's multi-contact design, the canted coil spring is able to maintain its position with little to no spring rolling. This allows for better control of insertion/removal forces as well as slip prevention in rotary applications.

Figures 29A, 29B:
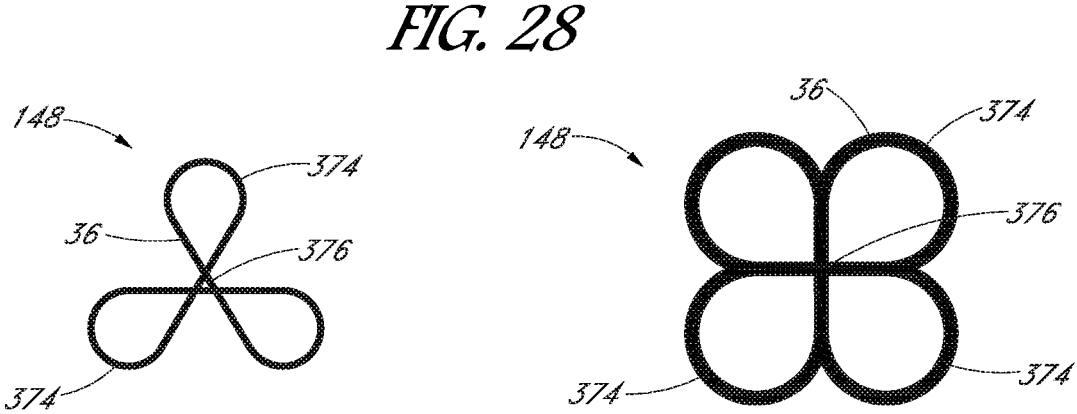
FIGS. 29A and 29B show cross-sectional views canted coil springs with coils having multi-loop geometry wherein said multi-loop geometry comprises multiple tear drop shaped loops, each comprising a tear drop tip, wherein each tear drop tip generally converges to the same point when viewing the cross-sectional profile.

FIGS. 29A and 29B show cross-sectional views of two canted coil springs 148 each with a plurality of coils 36 (only one shown) and each coil with multi-loops 374 and each coil with a geometry that resembles a three-leaf clover or a four-leaf clover. Said multi-loop geometry comprises multiple tear drop shaped loops 374, each comprising a tear drop tip 376, wherein each tear drop tip generally converges to the same point when viewing the cross-sectional profile. Due to the unique cross-sectional shape of the canted coil springs, the number of total contact points between piston and the canted coil spring 148 and between the housing and the canted coil spring 148 when used in a connector assembly may increase to 3 (in FIG. 29A) or 4 (FIG. 29B). These springs with multi-contacts are especially advantageous in electrical applications, where more contact points are desired for better electrical conductivity. Due to the canted coil springs' multi-contact design, the canted coil springs are able to maintain their position with little to no spring rolling. This allows for better control of insertion/removal forces as well as slip prevention in rotary applications.

In the following exemplary connector assemblies, a section of a connector housing is shown having a canted coil spring located therein. The connector housing may be one of the multi-part housings shown in FIGS. 1-18 in which at least one of the housing sections is formed by stamping and having a shape formed by cold working a blank with a die. The connector housing and spring are both understood to be annular and is configured to receive a pin, as shown in FIGS. 1, 2, and 5-8 or project into a bore of an external housing, as shown in FIGS. 10, 11, and 14-17. The pin and the external housing having the bore are not shown for clarity and can include a pin groove or an inside housing groove, respectively. Further, the housing groove can have different groove shapes than shown, such as having a V-bottom as shown in FIG. 5, tapered sidewalls, chamfered sidewalls with a lip, a single tapered bottom surface with a sidewall as shown in FIG. 8, etc.

With reference now to FIG. 30, a canted coil spring 148 comprising a plurality of coils 36 (only one shown) is shown located in a housing groove 140 of a connector housing 130, which is formed by attaching two housing sections 100 together and welding a seam or parting line. The housing groove is generally square with a flat bottom and two parallel sidewalls and a groove width. The coil 36 has a major axis and a minor axis and is located within the groove 140 at a turned angle due to the major axis of the coil being wider than the width of the housing groove 140. Alternatively, the coils can have a pre-turned angle and the spring can be positioned in the housing groove and not contact the sidewalls of the housing groove, as shown.

FIG. 31 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 discussed with reference to FIG. 19A and comprises one or more straight coil segments 170. The coil 36 is non-elliptical and non-rectangular in shape. At least one of the straight coil segments 170 contact the flat bottom surface of the housing groove 140 to increase contact surface areas, such as from one or more points to a line contact.

FIG. 32 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 discussed with reference to FIG. 19B and comprises one or more straight coil segments 170. The coil 36 is non-elliptical and non-rectangular in shape. One or two straight coil segments 170 can contact the sidewalls. The coil height of the present coil is increased and the plurality of coils are configured to cant along the coil height, which in the present embodiment is the longer of the two axes and perpendicular to lengthwise axis of the shaft, which is parallel to the bottom surface of the housing groove shown.

FIG. 33 shows a canted coil spring 148 comprising a plurality of coils 36 of different shapes and sizes located in a housing groove 140 of a connector housing 130, which is formed by attaching two housing sections 100 together and welding a seam or parting line. The housing groove 140 is generally square with a flat bottom and two parallel sidewalls and a groove width. The coils 36 comprise a first loop 380, a second loop 382, which is smaller than the first loop, and a third loop 384, which is smaller than the second loop. The coils 36 can repeat in this pattern and can include other loops and/or other patterns. The first and second loops 380, 382 are sized and arranged so that a lower base segment 388 of each loop contacts the flat bottom of the housing groove 140. The third loop 384 is spaced from the housing groove and can be employed to control the spring force or biasing force on the housing and/or the pin. For example, while the number of coils may be the same as other canted coil springs, i.e., coil density, the number of coils that contact the housing and/or the pin can be altered by changing the sizes to control how many coils that actually contact. The spring ring can be made smaller with the present canted coil spring as fewer coils are arranged along the spring inside spring diameter, which allows the garter ring to decrease in size.

FIG. 34 shows a canted coil spring 148 comprising a plurality of coils 36 of different shapes and sizes located in a housing groove 140 of a connector housing 130, which is formed by attaching two housing sections 100 together and welding a seam or parting line. The housing groove 140 is generally square with a flat bottom and two parallel sidewalls and a groove width. The coils 36 comprise a first loop 380 and a second loop 382, which is smaller than the first loop. The coils 36 can repeat in this pattern and can include other loops and/or other patterns. The first and second loops 380, 382 are sized and arranged so that a lower base segment 388 of each loop contacts the flat bottom of the housing groove 140. The first loop 380 can contact the sidewalls of the housing groove or be spaced therefrom, like the second loop 382. In the present embodiment, all coils can contact the housing groove but only about 50% of the coils touch the pin. For example, only the coils represented by the first loop 380 will touch the pin when the pin is inserted into the spring opening. The spring ring can be made smaller with the present canted coil spring as fewer coils are arranged along the spring inside spring diameter, which allows the garter ring to decrease in size.

FIG. 35 shows a canted coil spring 148 comprising a plurality of coils 36 of different shapes and sizes located in a housing groove 140 of a connector housing 130, which is formed by attaching two housing sections 100 together and welding a seam or parting line. The housing groove 140 is generally square with a flat bottom and two parallel sidewalls and a groove width. The coils 36 comprise a first loop 380, a second loop 382, which is smaller than the first loop, and a third loop 384, which is about the same size as the second loop. The coils 36 can repeat in this pattern and can include other loops and/or other patterns. The first loop 380 is sized and arranged so that a lower base segment 388 of each loop contacts the flat bottom of the housing groove 140 and the upper base segment 390 contacts the pin, when the pin is inserted into the ring opening of the canted coil spring 148. The second loop 382 is arranged to contact the pin like the first loop, but not the housing. The third loop 384 is arranged to contact the housing groove like the first loop, but not the pin. The spring ring can be made smaller with the present canted coil spring as fewer coils are arranged along the spring inside spring diameter, which allows the garter ring to decrease in size. Further, by controlling the number of coils that contact the pin and/or the housing, the spring force can be varied.

FIG. 36 shows a canted coil spring 148 comprising a plurality of coils 36 arranged laterally to increase the overall width of the spring. Two interior loops 336 are provided for every three coils 36, which can all be of the same shape and size but in other examples can be different. The spring 148 is located in a housing groove 140 of a connector housing 130, which is formed by attaching two housing sections 100 together and welding a seam or parting line. The housing groove 140 is generally square with a flat bottom and two parallel sidewalls and a groove width. Unlike the spring 148 of FIG. 32 in which the coil height CH of each coil is increased, in the present embodiment, the coils are staggered to increase the coil width CW and the groove width is increased accordingly to accommodate the canted coil spring 148. The staggered coils can repeat in this pattern and can include other loops and/or other patterns.

FIG. 37 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is triangular in shape with rounded corners 394. The coil 36 can have equal sides and therefore having angle $\alpha$ and angle $\beta$ that are about the same. A lower straight segment 270 of the coil 36 can contact the flat bottom of the housing groove 140. The coil 36 is non-elliptical and non-rectangular in shape. Two or three of the sides of the triangular shaped coil can change to vary angles $\alpha$ and $\beta$ to vary insertion and disconnect forces, as described elsewhere herein.

FIG. 38 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is triangular in shape with rounded corners 394. The coil 36 is non-elliptical and non-rectangular in shape. The coil 36 can be a right triangle in which the angles $\alpha$ and $\beta$ are about the same. However, the triangle can be other than a right triangle and the sides are not equal in length to vary angles $\alpha$ and $\beta$. A lower straight segment 270 of the coil 36 can contact the flat bottom of the housing groove 140. The shape of the coil 36 can be modified to vary angles $\alpha$ and $\beta$ to vary insertion and disconnect forces, as described elsewhere herein.

FIG. 39 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is generally square in shape with rounded corners 394. The coil 36 can instead be rectangular in shape. A lower straight segment 270 of the coil 36 can contact the flat bottom of the housing groove 140. The shape of the coil 36 can be modified to vary angles $\alpha$ and $\beta$ to vary insertion and disconnect forces, as described elsewhere herein.

FIG. 40 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 may be considered a rhombus shape with rounded corners 394 and with equal side segments. The coil 36 is non-elliptical and non-rectangular in shape. The coil 36 can instead have different side lengths to vary the coil height and/or coil width to vary angles α and β to vary insertion and disconnect forces, as described elsewhere herein.

FIG. 41 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 may be considered a pentagonal shape with rounded corners 394 and similar to the coil 36 shown with reference to FIG. 23E. The coil 36 is non-elliptical and non-rectangular in shape. The coil 36 can have different side lengths to vary the coil height and/or coil width to vary angles α and β to vary insertion and disconnect forces, as described elsewhere herein.

FIG. 42 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 may be considered a convex polygon in shape with rounded corners 394 and similar to the coil 36 shown with reference to FIG. 23C. The coil 36 is non-elliptical and non-rectangular in shape. The coil 36 can have different side lengths to vary the coil height and/or coil width to vary angles α and β to vary insertion and disconnect forces, as described elsewhere herein.

FIG. 43 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 may be considered a five sided polygon with rounded corners 394 and similar to the coil 36 shown with reference to FIG. 23E. The coil 36 is non-elliptical and non-rectangular in shape. The coil 36 can have different side lengths to vary the coil height and/or coil width to vary angles α and β to vary insertion and disconnect forces, as described elsewhere herein.

FIG. 44 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 may be considered a five sided polygon with rounded corners 394 and similar to the coil 36 shown with reference to FIG. 28. The coil 36 is non-elliptical and non-rectangular in shape. As shown, the coil has a star-shaped geometry with the wire of the canted coil spring following a pentagram pattern. The coil 36 can have different side lengths to vary the coil height and/or coil width, as described elsewhere herein.

FIG. 45 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 has generally parallel straight segments 270 each joined by elliptical segments 272 and arranged in a "T" shape. The coil 36 is non-elliptical and non-rectangular in shape. The coil 36 has straight segments 270 to form line contacts and can increase surface contact areas with the bottom surface of the housing groove 140.

FIG. 46 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 26D. The coil 36 is non-elliptical and non-rectangular in shape. The "X" shape of the coil 36 gives it a wide working range of deflection. The "X" shape of the coil 36 also provides multiple spaced apart contacts with the bottom surface of the housing groove.

FIG. 47 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 29A.

FIG. 48 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 29B.

FIG. 49 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 24.

FIG. 50 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 26A.

FIG. 51 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 26B.

FIG. 52 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 shown has four sides 400, including at least one straight segment 270 for forming a line contact with a groove bottom of the housing groove 140. As shown, the straight segment 270 is connected to two side segments 402 at right angles. The two side segments 402 can have equal lengths as shown or can have unequal lengths. The upper segment 404 opposite the straight bottom segment 270 can be curved or arcuate and connects to the two side segments 402. The curved upper segment can project away from the housing groove bottom surface. The two side segments can be straight as shown or each can include a curved section. The coil 36 can have equal sides and therefore having angle α and angle β that are about the same. The coil 36 is non-elliptical and non-rectangular in shape. Two or three of the sides of the coil can change to vary angles α and β to vary insertion and disconnect forces, as described elsewhere herein. The curved upper segment 404 facilitates insertion of a pin and the equal sides 402 produce generally similar insertion and removal forces when the spring 146 is used with a pin. Thus, an aspect of the present coil 36 is understood to include three or more straight segments and wherein two of the three straight segments are side segments and one of the three straight segments is a bottom segment joining the two side segments, and wherein a curved upper segment joins the two side segments, such as at a location opposite the bottom segment.

FIG. 53 shows a canted coil spring 148 comprising a plurality of coils 36 (only one shown) located in a housing groove 240 of a connector housing 230, which is formed by attaching two housing sections 200 together and welding a seam or parting line. The connector housing 230 is similar to the housing of FIG. 10 and is configured for projecting into a bore an exterior housing. Alternatively, the connector housing 230 can be similar to the connector housing of FIG. 1. The housing groove 240 is generally square with a flat bottom and two parallel sidewalls and a groove width. The coil 36 is generally elliptical and has a major axis and a minor axis and is located within the groove 240 the combination housing and spring configured to be inserted into a bore of an external housing, similar to the assembly shown in FIGS. 10 and 11. In the present embodiment, a dimple 410 is formed on the coil 36 to create an inwardly arc section to thereby form two contact points 412, 414 when the coil contacts a flat surface area, such as an interior surface of a bore of an external groove. Thus, an aspect of the present disclosure is understood to include a multi-part housing having at least two housing sections and wherein at least one of the housing sections is formed by stamping and the section has a bend or a curved surface formed by pressing the surface against a die. As shown, two such housing sections are used and attached together to form a housing groove for accommodating a canted coil spring comprising plurality of coils and wherein at least several of the coils each comprises a dimple. The dimple 410 defines a low area or region of the coil, such as a concave arc region, in between two raised regions to form two contact points 412 414 when the coil contacts a flat surface area.

FIG. 54 shows a canted coil spring 148 comprising a plurality of coils 36 (only one shown) located in a housing groove 240 of a connector housing 230, which is formed by attaching two housing sections 200 together and welding a seam or parting line. The connector housing 230 is similar to the housing of FIGS. 14 and 15 and is configured for projecting into a bore of an exterior housing. Alternatively, the connector housing 230 can be similar to the connector housing of FIG. 1. The housing groove is generally V-shape and has two sidewalls. The coil 36 is similar to the coil 36 of FIG. 53 and has a dimple 410 defining two contact points when the coil contacts a flat surface area.

FIG. 55 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 30 and has a major axis and a minor axis. The coil is turned when positioned in the housing groove and has a major axis that is wider than the groove width. The coil has a dimple 410 defining two contact points 412, 414 when the coil contacts a flat surface.

FIG. 56 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 31 and has a dimple 410 defining two contact points 412, 414 when the coil contacts a flat surface.

FIG. 57 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 32 and has a dimple 410 defining two contact points 412, 414 when the coil contacts a flat surface.

FIG. 58 shows a canted coil spring 148 comprising a plurality of coils 36 located in a housing groove 140 of a connector housing 130, which is formed by attaching two housing sections 100 together and welding a seam or parting line. The housing groove is generally square with a flat bottom and two parallel sidewalls and a groove width. The coils 36 are similar to the coils 36 shown with reference to FIG. 34 and one of the coil loop has a dimple 410 defining two contact points 412, 414 when the coil contacts a flat surface.

FIG. 59 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 37 and one of the sides has a dimple 410 defining two contact points 412, 414 when the coil contacts a flat surface.

FIG. 60 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 38 and one of the sides has a dimple 410 defining two contact points 412, 414 when the coil contacts a flat surface.

FIG. 61 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 39 and one of the sides has a dimple 410 defining two contact points 412, 414 when the coil contacts a flat surface.

FIG. 62 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 40 and one of the sides has a dimple 410 defining two contact points 412, 414 when the coil contacts a flat surface. The coil 36 also resembles a heart shape.

FIG. 63 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 41 and one of the sides has a dimple 410 defining two contact points 412, 414 when the coil contacts a flat surface.

FIG. 64 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 42 and one of the sides has a dimple 410 defining two contact points 412, 414 when the coil contacts a flat surface.

FIG. 65 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 43 and one of the sides has a dimple 410 defining two contact points 412, 414 when the coil contacts a flat surface.

FIG. 66 shows a canted coil spring 148 comprising a plurality of coils 36 located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIGS. 47 and 29A and has multiple loops 374 forming a three-leaf clover-like shape. In the present embodiment, one of the loops has a dimple 410 defining two contact points 412, 414 when the coil contacts a flat surface.

FIG. 67 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 49 and has two dimples, a first dimple 338 formed by an internal loop 336, as previously described, and a second dimple 410 on one of the sides of the coil 36 to define two contact points 412, 414 with the flat surface of the housing groove. The side of the coil with the first dimple 338 can contact a flat surface to create two contact points or can engage a convex projection on a pin to form a latching connection.

FIG. 68 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 26A and has two dimples, a first dimple 338 formed by an internal loop 336, as previously described, and a second dimple 410 on one of the sides of the coil 36 to define two contact points 412, 414 with the flat surface of the housing groove. The side of the coil with the first dimple 338 can contact a flat surface to create two contact points or can engage a convex projection on a pin to form a latching connection.

FIG. 69 shows a canted coil spring 148 comprising a plurality of coils 36 (only one shown) located in a housing groove 140 of a connector housing 130, which is formed by attaching two housing sections 100 together and welding a seam or parting line. The housing groove is generally square with a flat bottom and two parallel sidewalls and a groove width. The coil 36 is similar to the coil 36 shown with reference to FIG. 52 and the curved side 404 has a dimple 410 defining two contact points 412, 414 when the coil contacts a flat surface. The lower side has a straight segment 270 for contacting the groove bottom of the housing groove along a line contact.

The present disclosure is further understood to include methods for making and for using any one or more of the various connector assemblies and connector components discussed herein.

Although limited embodiments of stamped housing sections and canted coil springs and their components have been specifically described and illustrated herein, many modifications and variations will be apparent to those skilled in the art. Furthermore, elements and features expressly discussed for one embodiment but not for another may equally apply provided the functionality or structures do not conflict. Thus, unless the context indicates otherwise, like features for one embodiment are applicable to another embodiment. Accordingly, it is to be understood that the housing sections, the canted coil springs and their components constructed according to principles of the disclosed device, system, and method may be embodied other than as specifically described herein. The disclosure is also defined in the following claims.

What is claimed is:
1. A connector assembly comprising:
a connector housing comprising a first housing section made at least in part by stamping attached to a second housing section made at least in part by stamping and having an interior cavity with a housing groove;
a canted coil spring having a plurality of coils that cant generally in a same direction located in the housing groove;
wherein the first housing section comprises a first bottom wall with an endmost surface and a first sidewall extending from the first bottom wall at an angle;
wherein the second housing section comprises a second bottom wall with an endmost surface and a second sidewall extending from the second bottom wall at an angle;

wherein the first bottom wall and the second bottom wall define a groove bottom of the housing groove and the first sidewall and the second sidewall define two sidewalls of the housing groove;

wherein the endmost surfaces of the first housing section and second housing sections are welded together end-to-end in a butt-joint or end-to-end with endmost surfaces that are angled to one another to form the connector housing having two opening; and wherein the angle of the first housing section is an acute angle or an obtuse angle.

2. The connector assembly of claim 1, wherein the first housing section and the second housing section are substantially identical.

3. The connector assembly of claim 1, wherein the two openings align to receive a pin.

4. The connector assembly of claim 1, further comprising a canted coil spring located in the housing groove, wherein the canted coil spring comprises a plurality of coils and wherein each of the plurality of coils comprises a dimple.

5. The connector assembly of claim 4, wherein the coils with the dimples each comprises a straight segment.

6. The connector assembly of claim 1, wherein the angle of the second housing section is a right angle, an acute angle, or an obtuse angle.

7. The connector assembly of claim 6, wherein the canted coil spring comprises a plurality of coils each with three or more straight segments and defining an angle α and angle β between the three or more straight segments.

8. The connector assembly of claim 7, wherein a base of each of the plurality of coils has a straight segment for forming a line contact with a bottom surface of the housing groove.

9. The connector assembly of claim 8, further comprising a dimple on a segment of each of the plurality of coils for forming two contact points at each of the plurality of coils.

10. The connector assembly of claim 7, wherein angle α is greater than angle β or angle α is less than angle β.

11. The connector assembly of claim 10, wherein angle α is at least two straight segments separated from angle β, and angle α is greater than angle β or angle α is less than angle β.

12. A connector assembly comprising:

a connector housing comprising an interior cavity with a housing groove therein; and a canted coil spring with complex coil shape comprising a continuous plurality of coils and a spring axis through said coils; each coil comprising a coil shape and a cross-sectional axis and canted about said cross-sectional axis; said coil shape comprising a polygonal geometry; said canted coil spring with polygonal geometry being received in the housing groove;

wherein the polygonal geometry coil shape comprises a plurality of straight segments with two adjacent straight segments having an angle therebetween consisting of an acute angle or an obtuse angle;

wherein the polygonal geometry comprises a five sided geometry with a first segment, a second segment, a third segment, a fourth segment, and a fifth segment;

wherein the first segment and the second segment are each arranged at a right angle to the third segment; and wherein the first segment and the fourth segment define an angle α and the second segment and the fifth segment define an angle β.

13. The connector assembly of claim 12, wherein the cross-sectional axis is generally parallel to a straight segment of said polygonal geometry of said coil shape.

14. The connector assembly of claim 12, wherein fourth segment is longer than the fifth segment.

15. The connector assembly of claim 12, wherein the fourth segment and fifth segment are approximately equal in length.

16. The connector assembly of claim 12, an angle between the fourth segment and the fifth segment is an acute angle.

17. The connector assembly of claim 12, further comprising a dimple form on one of the segments.

18. The connector assembly of claim 12,
wherein the connector housing comprises a first housing section attached to a second housing section having a seam located at a groove bottom of the housing groove.

19. The connector assembly of claim 18, wherein angle α is greater than angle β or angle α is less than angle β.

\* \* \* \* \*